US012638447B2

(12) United States Patent　　　　(10) Patent No.: US 12,638,447 B2
Brown et al.　　　　　　　　　　　(45) Date of Patent: May 26, 2026

(54) **COMPOSITIONS, METHODS, AND SYSTEMS FOR DETECTING METHICILLIN-RESISTANT *STAPHYLOCOCCUS AUREUS***

(71) Applicant: Laboratory Corporation of America Holdings, Burlington, NC (US)

(72) Inventors: Matthew J. Brown, Burlington, NC (US); Minh Mindy Bao Nguyen, Shoreview, MN (US); Stephen Erickson, White Bear Township, MN (US); Jose Gil, Winnetka, CA (US)

(73) Assignee: Laboratory Corporation of America Holdings, Burlington, NC (US)

( * ) Notice: Subject to any disclaimer, the term of this patent is extended or adjusted under 35 U.S.C. 154(b) by 183 days.

(21) Appl. No.: 17/245,584

(22) Filed: Apr. 30, 2021

(65) Prior Publication Data

US 2021/0341477 A1　　Nov. 4, 2021

Related U.S. Application Data

(60) Provisional application No. 63/018,081, filed on Apr. 30, 2020.

(51) Int. Cl.
*G01N 33/569* (2006.01)
*G01N 33/68* (2006.01)

(52) U.S. Cl.
CPC ....... *G01N 33/56938* (2013.01); *G01N 33/68* (2013.01); *G01N 2333/005* (2013.01)

(58) Field of Classification Search
CPC ............. G01N 33/56938; G01N 33/68; G01N 2333/005
See application file for complete search history.

(56) References Cited

U.S. PATENT DOCUMENTS

| | | | |
|---|---|---|---|
| 2004/0038307 A1* | 2/2004 | Lee .......................... | C12Q 1/48 435/7.1 |
| 2015/0218616 A1 | 8/2015 | Anderson et al. | |
| 2019/0010534 A1 | 1/2019 | Nguyen et al. | |

FOREIGN PATENT DOCUMENTS

| | | |
|---|---|---|
| CN | 102131915 A | 7/2011 |
| CN | 110869511 A | 3/2020 |
| JP | 2006511819 A | 4/2006 |
| JP | 2016521996 A | 7/2016 |
| WO | 2004046164 A2 | 6/2004 |
| WO | 2018126266 A1 | 7/2018 |
| WO | 2019010177 A1 | 1/2019 |
| WO | 2019/209982 | 10/2019 |
| WO | 2019209982 A1 | 10/2019 |

OTHER PUBLICATIONS

"Anti-NanoLuc® Monoclonal Antibody," Available online At: https://www.promega.in/products/protein-detection/primary-and-secondary-antibodies/anti-nanoluc-monoclonal-antibody/?catNum=N7000, XP055829353, Feb. 1, 2020, 7 pages.
"NanoLuc® (Nluc) Luciferase Antibody," Available online At: https://www.rndsystems.com/products/nanoluc-nluc-luciferase-antibody-965853_mab100261, XP055829366, Jul. 2, 2019, 6 pages.
Brown, M. et al., "Development and Evaluation of a Sensitive Bacteriophage-Based MRSA Diagnostic Screen," Viruses, 12:631 (2020), 15 pages.
PCT/US2021/030127, International Search Report and Written Opinion, Aug. 11, 2021, 14 pages.
CA Application No. 3181416 , "Office Action", Mar. 6, 2024, 5 pages.
International Applicatoin No. PCT/US2021/030127 , "International Preliminary Report on Patentability", Nov. 10, 2022, 10 pages.
Office Action issued in CA 3181416 dated Mar. 11, 2025, 4 pages.
Office Action issued in CA 3181416 dated Mar. 6, 2024, 5 pages.
Office Action issued in CN 202180043564.1 dated Apr. 11, 2025, 21 pages.
Intention to Grant issued in EP 21727310.1 dated Jul. 3, 2025, 9 pages.
Office Action issued in JP 2022-565846 dated May 16, 2025, 7 pages.
International Preliminary Report on Patentability issued in PCT/US2021/030127 dated Nov. 10, 2022, 10 pages.
Anonymous: "Certificate of Analysis Anti-Nano Luc Monoclonal Antibody", Feb. 1, 2020 (Feb. 1, 2020), XP055829353, Retrieved from the Internet: URL:https://nld.promega.com/products/protein-detection/primary-and-secondary-antibodies/anti-nanoluc-monoclonal-antibody/?catNum=N7000 [retrieved on Aug. 2, 2021].
Anonymous: "NanoLuc (Niue) Luciferase Antibody datasheet, Monoclonal Mouse IgG2A Clone# 965853 Catalog No. MAB100261, from R&D Sytems", Jul. 2, 2019 (Jul. 2, 2019), XP055829366, Retrieved from the Internet: URL:https://resources.rndsystems.com/pdfs/datasheets/mab100261.pdf? V=20210802&_ga=2. 219606683. 342248463 .1627887 455-172037157 .1627 887455 [retrieved on Aug. 2, 2021].

* cited by examiner

*Primary Examiner* — Robert A Zeman
(74) *Attorney, Agent, or Firm* — Kilpatrick Townsend & Stockton LLP

(57) ABSTRACT

Disclosed are compositions, methods and systems for detecting MRSA, for example MRSA nasal colonization. In certain embodiments, the methods use bacteriophage-based amplification of the signal in detection of bacteria and other microorganisms to detect MRSA. The methods for detecting MRSA may include preparing an assay comprising a selective agent and a cocktail comprising at least two different types of recombinant bacteriophages, incubating the sample in the assay, capturing an indicator protein product, and detecting an indicator protein product produced by the recombinant bacteriophage, wherein positive detection of the indicator protein product indicates that MRSA is present in the sample.

11 Claims, No Drawings

COMPOSITIONS, METHODS, AND SYSTEMS FOR DETECTING METHICILLIN-RESISTANT *STAPHYLOCOCCUS AUREUS*

CROSS-REFERENCE TO RELATED APPLICATION

This application claims priority to and the benefit of U.S. Provisional Application No. 63/018,081, filed Apr. 30, 2020, which is incorporated herein by reference in its entirety

FIELD

The present disclosure relates to compositions, methods and systems for detecting Methicillin-resistant *Staphylococcus aureus* (MRSA) using infectious agents.

BACKGROUND

There is a strong interest in detecting bacteria and other microorganisms that can cause various forms of debilitating and fatal infection. Bacterial pathogens can cause substantial morbidity among humans and domestic animals, as well as immense economic loss.

Specifically, Methicillin-resistant *Staphylococcus aureus* (MRSA) is a critically important human pathogen with the capacity to cause fatal infections. MRSA is a leading cause of surgical site infections in hospitals, associated with longer patient stays, higher rates of readmission, decreased survival rates, and economic loss. Because of the profound clinical and financial burden to the healthcare industry, significant efforts have been made to understand and control the source of MRSA-related infections. Nasal carriage of MRSA has been found to be a major risk factor for subsequent disease and the majority of *Staphylococcus aureus* infections can be matched to endogenous colonizing strain. Elimination of this risk factor through decolonization of MRSA nasal carriers has proven to be a successful strategy in reducing surgical site infection.

Traditional microbiological tests for detecting MRSA rely on non-selective and selective enrichment cultures followed by plating on selective media and further testing to confirm suspect colonies from patient nasal swab specimens. Culture-based methods of detection may involve the use of chromogenic and selective agar and often demonstrate strong performance in regards to sensitivity and specificity. While often significantly cheaper than some methods, one major drawback of culture-based methods is that results typically require 18 to 24 hours of incubation before detection.

A variety of rapid methods have been investigated and introduced into practice to reduce the time for testing. However, these methods also have drawbacks. For example, techniques involving immunoassays or gene probes generally require an enrichment step in order to obtain adequate sensitivity. Polymerase chain reaction (PCR) tests also include an amplification step and therefore are capable of both very high sensitivity and selectivity. Detection of MRSA-specific DNA sequences with real-time PCR has demonstrated excellent sensitivity and specificity, rapid time to results, and overall clinical effectiveness. While real-time PCR has yielded promising results, this method also has drawbacks. First, new generations of real-time PCR must constantly be developed to match the changing genetic landscape of MRSA resistance as previous PCR has resulted in the failure of some assays to detect novel MRSA strains.

Secondly, relative to culture-based alternatives, the high cost of real-time PCR has led to uncertainty regarding cost-effectiveness, particularly in regions with low endemic carriage rates.

Therefore, there is a need for more rapid, simple and sensitive detection and identification of MRSA.

BRIEF SUMMARY

Embodiments of the present disclosure comprise compositions, methods, apparatuses, systems, and kits for the detection of MRSA nasal colonization. The present disclosure may be embodied in a variety of ways.

In some embodiments, the present disclosure provides a method for detecting Methicillin-resistant *Staphylococcus aureus* (MRSA) in a sample. The method comprises: obtaining a sample; adding a selective agent to the sample; contacting the sample with a cocktail comprising one or more infectious agents, wherein the infectious agent comprises an indicator gene and is specific to *Staphylococcus aureus*, and wherein the indicator gene encodes an indicator protein product; capturing the indicator protein product; and detecting a signal produced by the indicator protein product, wherein detection of the signal is used to determine the presence of MRSA in the sample.

In some embodiments, the present disclosure provides a method for detecting a microorganism in a sample. The method comprises obtaining a sample; contacting the sample with a cocktail comprising one or more infectious agents, wherein the infectious agent comprises an indicator gene and is specific to a microorganism, and wherein the indicator gene encodes an indicator protein product; contacting the indicator protein product with a surface, the surface comprising an immobilized binding partner for capturing the indicator protein product; and detecting a signal produced by the indicator protein product, wherein detection of the signal is used to determine the presence of the microorganism in the sample.

In some embodiments, the present disclosure utilizes novel recombinant bacteriophage for detecting MRSA from nasal swab specimens. In some embodiments, the novel recombinant bacteriophage is specific to *Staphylococcus aureus*. A novel diagnostic screen utilizes an assay comprising recombinant bacteriophage including luciferase reporters capable of recognizing *Staphylococcus aureus*, while relying on an antibiotic to restrict growth of non-MRSA stains. A variety of MRSA strains can be detected using the methods described herein.

In some embodiments, the disclosure provides methods of detecting MRSA from a sample comprising: (a) contacting the sample with a selective agent, (b) contacting the sample with a cocktail comprising one or more infectious agents, wherein the infectious agent comprises an indicator gene and is specific to *Staphylococcus aureus*, and wherein the indicator gene encodes an indicator protein product, and (c) detecting a signal produced by an indicator protein product, wherein detection of the signal is used to determine the concentration of MRSA in the sample. In some embodiments, the selective agent comprises an antibiotic (e.g., cefoxitin). In some embodiments, the sample is derived from a nasal swab.

In some embodiments, the infectious agent is a recombinant phage that is specific to is specific to *Staphylococcus aureus* bacterium. In further embodiments, the indicator gene encodes the indicator protein product that generates an intrinsic signal or an enzyme that generates signal upon reaction with substrate.

In some embodiments, the present disclosure provides a method for detecting MRSA from a sample comprising: contacting the sample with a selective agent, wherein the sample is derived from a nasal swab; contacting the sample with a cocktail comprising one or more infectious agents, wherein the infectious agent comprises an indicator gene and is specific to *Staphylococcus aureus*, and wherein the indicator gene encodes an indicator protein product, and detecting a signal produced by an indicator protein product, wherein detection of the signal is used to determine the presence of MRSA in the sample.

In some embodiments, the present disclosure provides a method for detecting in a sample comprising: obtaining a sample; adding a selective agent to the sample; contacting the sample with a cocktail comprising one or more infectious agents, wherein the infectious agent comprises an indicator gene and is specific to *Staphylococcus aureus*, and wherein the indicator gene encodes an indicator protein product; capturing the indicator protein product; and detecting a signal produced by the indicator protein product, wherein detection of the signal is used to determine the presence of MRSA in the sample.

In some embodiments, the present disclosure provides a kit and a system for detecting MRSA comprising nasal swab; and an assay comprising a recombinant bacteriophage that is specific to *Staphylococcus aureus* and an antibiotic solution. In some embodiments, the kit comprises a nasal swab; an assay comprising a recombinant bacteriophage that is specific to *Staphylococcus aureus* and optionally an antibiotic; and a surface for capturing an indicator protein product.

Certain specific embodiments of the present disclosure make use of methods and construct described in US Patent Publication No. 2015/0218616, which is incorporated by reference herein in its entirety.

DETAILED DESCRIPTION

Disclosed herein are compositions, methods and systems that demonstrate surprising sensitivity for detecting a variety of strains of Methicillin-resistant *Staphylococcus aureus* (MRSA) in test samples (e.g., biological samples) in a shorter timeframe than conventional methods. The compositions, methods and systems disclosed herein can detect MRSA in a shorter timeframe than was previously thought possible using genetically modified infectious bacteriophage with reduced time for culturing for enrichment, or in some embodiments, with minimal incubation times during which MRSA could potentially multiply. Surprisingly, an assay using one or more recombinant bacteriophage in the presence of an antibiotic (e.g., cefoxitin), for incubation with a test sample, detects a variety of MRSA strains at concentrations that generate very low numbers of colony-forming units (CFU). Such low CFU concentrations were previously purported to be detected only after using culture-based methods that require incubation for over 24 hours. However, the assay described herein can facilitate finding, binding, and infecting a low number of target cells. In some embodiments, the assay detects MRSA from nasal swab specimens in less than ten hours at costs similar to lengthier culture-based methods.

In some aspects, the bacteriophage-based MRSA assay described herein provide specific, sensitive, rapid, and low-cost detection of target bacteria and address growing diagnostic needs in multiple industries. Specifically, detecting MRSA nasal colonization and antibiotic susceptibility play a critical supportive role in preventing hospital-acquired infections and facilitating antibiotic stewardship. In some embodiments, the bacteriophage-based MRSA assay for nasal swab specimens utilizes two luciferase reporter phages capable of recognizing genetically-diverse *Staphylococcus aureus*. In some embodiments, a beta-lactam antibiotic, cefoxitin, is included to differentiate between resistant (MRSA) and susceptible organisms. The bacteriophage-based MRSA assay surprisingly positively identifies MRSA isolates at low bacterial concentrations, and at higher inoculums, non-MRSA *Staphylococcus aureus* yielded appropriate negative results. Additionally, cross-reactivity of the phage cocktail with other *staphylococcal* and *bacillus* species can be mitigated under selective conditions. Thus, the bacteriophage-based MRSA assay described herein sensitively detect MRSA both in vitro and in human nasal matrix.

In some aspects, the present disclosure provides a recombinant bacteriophage comprising an indicator gene inserted into a late gene region of a bacteriophage genome. In some embodiments, the recombinant bacteriophage is a genetically modified *Staphylococcus aureus*-specific bacteriophage genome. In certain embodiments, the recombinant bacteriophage comprises a genetically modified bacteriophage genome derived from a bacteriophage that specifically recognizes *Staphylococcus aureus*. In some embodiments, a cocktail of bacteriophage comprises at least two different types of recombinant bacteriophages derived from bacteriophage that specifically recognizes *Staphylococcus aureus*. In some embodiments, an assay including a cocktail of recombinant bacteriophage and a selective agent (e.g., an antibiotic) can distinguish MRSA in the presence of other types of bacteria, specifically, Methicillin-sensitive *Staphylococcus aureus* (MSSA).

In some aspects, a method for detecting MRSA may use an infectious agent for detecting *Staphylococcus aureus*. For example, in certain embodiments, the microorganism of interest is MRSA and the infectious agent is a bacteriophage that specifically infects *Staphylococcus aureus*. Thus, in certain embodiments, the method may comprise selecting one or more bacteriophages that specifically infect *Staphylococcus aureus* bacterium, preparing a recombinant bacteriophage derived from a *Staphylococcus aureus* bacteriophage, preparing an assay comprising the recombinant bacteriophage and a selective agent (e.g., an antibiotic), and providing a sample from a nasal swab or similar source for analysis in the assay. In certain embodiments, the recombinant bacteriophage comprises an indicator gene. In certain embodiments, the indicator gene may be inserted into a late gene region of the bacteriophage such that expression of the indicator gene during bacteriophage replication following infection of host bacteria results in production of an indicator protein product. The method may comprise detecting the indicator protein product, wherein positive detection of the indicator protein product indicates that MRSA is present in the sample. In some embodiments, the indicator protein is soluble.

In some embodiments, compositions, methods and systems can detect MRSA from diverse genetic backgrounds using an assay comprising one or more recombinant bacteriophage and a selective agent, e.g., an antibiotic. In some embodiments, the assay utilizes a selective agent, e.g., cefoxitin, to restrict the viability of susceptible bacteria, while allowing growth of MRSA. For example, the selective agent may kill or decrease growth of all *Staphylococcus aureus* bacterium (e.g., MSSA) other than MRSA. In this way, cefoxitin is capable of identifying diverse isolates of MRSA from competitor organisms. As described herein, an assay including cefoxitin results in high selectively of MRSA, and importantly, does not interfere with detection of MRSA strains. Additionally, cefoxitin is effective in reducing false positives from several species of coagulase-negative *Staphylococci*.

In some embodiments, the methods and systems described herein selectively detect low levels of MRSA from a nasal swab or similar sample. Each of the embodiments of the methods and systems of the present disclosure can be applied to detection and quantification of a large variety MRSA strains. The methods and systems provide high detection sensitivity in a short time without the need for traditional biological enrichment and/or incubation that requires at least 24 hours. The method utilizes a novel bacteriophage-based MRSA diagnostic screen. This assay is a member of a new generation of luciferase-phage reporter systems utilizing a luciferase such as NANOLUC® to sensitively detect target species. The method proved to be highly inclusive and, when combined with cefoxitin selection, discriminates against the majority of non-resistant strains. Moreover, the screen was capable of identifying low burdens of MRSA in nasal samples with little or no interference.

In certain embodiments, the present disclosure may comprise a system. The system may contain at least some of the compositions of the present disclosure. In addition, the system may comprise at least some of the components for performing the method. In certain embodiments, the system is formulated as a kit. Thus, in some embodiments, a system for rapid detection of MRSA from a nasal swab, comprises: a component for incubating the sample with a recombinant infectious agent specific for the microorganism of interest, wherein the recombinant infectious agent comprises an indicator moiety; a selective agent; and a component for detecting the indicator moiety. In other embodiments, the present disclosure comprises software for use with the methods or systems.

Some embodiments of the present disclosure described herein utilize the discovery that a single microorganism is capable of recognizing and binding specific infectious agents, such as bacteriophage. Following infection and replication of the bacteriophage, the successful infection and generation of progeny phage may be detected via an indicator moiety expressed during bacteriophage replication. This principle allows amplification of indicator signal from one or a few cells based on specific recognition of microorganism surface receptors. For example, by exposing even a single cell of a bacterium to a plurality of bacteriophage, thereafter allowing amplification of the bacteriophage and high-level expression of an encoded indicator gene product during replication, the indicator signal is amplified such that the single bacterium is detectable.

Definitions

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well-known and commonly used in the art. Known methods and techniques are generally performed according to conventional methods well known in the art and as described in various general and more specific references that are discussed throughout the present specification unless otherwise indicated. Enzymatic reactions and purification techniques are performed according to manufacturer's specifications, as commonly accomplished in the art or as described herein. The nomenclatures used in connection with the laboratory procedures and techniques described herein are those well-known and commonly used in the art. The following terms, unless otherwise indicated, shall be understood to have the following meanings:

As used herein, the terms "a", "an", and "the" can refer to one or more unless specifically noted otherwise.

The use of the term "or" is used to mean "and/or" unless explicitly indicated to refer to alternatives only or the alternatives are mutually exclusive, although the disclosure supports a definition that refers to only alternatives and "and/or." As used herein "another" can mean at least a second or more.

Throughout this application, the term "about" is used to indicate that a value includes the inherent variation of error for the device, the method being employed to determine the value, or the variation that exists among samples.

The term "solid support" or "support" means a structure that provides a substrate and/or surface onto which biomolecules may be bound. For example, a solid support may be an assay well (i.e., such as a microtiter plate or multi-well plate), or the solid support may be a location on a filter, an array, or a mobile support, such as a bead or a membrane (e.g., a filter plate or lateral flow strip).

The term "binding agent" or "binding partner" refers to a molecule that can specifically and selectively bind to a second (i.e., different) molecule of interest. The interaction may be non-covalent, for example, as a result of hydrogen bonding, van der Waals interactions, or electrostatic or hydrophobic interactions, or it may be covalent.

The term "soluble binding agent" refers to a binding agent that is not associated with (i.e., covalently or non-covalently bound) to a solid support.

The term "immobilized binding partner" refers to a binding agent that is associated with (i.e., covalently or non-covalently bound) to a solid support.

As used herein, an "analyte" refers to a molecule, compound or cell that is being measured. The analyte of interest may, in certain embodiments, interact with a binding agent.

As described herein, the term "analyte" may refer to a protein or peptide of interest. An analyte may be an agonist, an antagonist, or a modulator. Alternatively, an analyte may not have a biological effect. Analytes may include small molecules, sugars, oligosaccharides, lipids, peptides, peptidomimetics, organic compounds and the like.

The term "detectable moiety" or "detectable biomolecule" or "reporter" or "indicator" or "indicator moiety," refers to a molecule that can be measured in a quantitative assay. For example, an indicator moiety may comprise an enzyme that may be used to convert a substrate to a product that can be measured. An indicator moiety may be an enzyme that catalyzes a reaction that generates bioluminescent emissions (e.g., luciferase). Alternatively, an indicator moiety may be a radioisotope that can be quantified. Alternatively, an indicator moiety may be a fluorophore. Alternatively, other detectable molecules may be used.

As used herein, "bacteriophage" or "phage" includes one or more of a plurality of bacterial viruses. In this disclosure, the terms "bacteriophage" and "phage" include viruses such as mycobacteriophage (such as for TB and paraTB), mycophage (such as for fungi), mycoplasma phage, and any other term that refers to a virus that can invade living bacteria, fungi, mycoplasma, protozoa, yeasts, and other microscopic living organisms and uses them to replicate itself. Here, "microscopic" means that the largest dimension is one millimeter or less.

Bacteriophages are viruses that have evolved in nature to use bacteria as a means of replicating themselves. A phage does this by attaching itself to a bacterium and injecting its DNA (or RNA) into that bacterium, and inducing it to replicate the phage hundreds or even thousands of times. This is referred to as phage amplification.

As used herein, "late gene region" refers to a region of a viral genome that is transcribed late in the viral life cycle. The late gene region typically includes the most abundantly expressed genes (e.g., structural proteins assembled into the bacteriophage particle). Late genes are synonymous with class III genes and include genes with structure and assembly functions. For example, the late genes (synonymous with class III,) are transcribed in phage T7, e.g., from 8 minutes after infection until lysis, class I (e.g., RNA polymerase) is early from 4-8 minutes, and class II from 6-15 minutes, so there is overlap in timing of II and III. A late promoter is one that is naturally located and active in such a late gene region.

As used herein, "culturing for enrichment" refers to traditional culturing, such as incubation in media favorable to propagation of microorganisms, and should not be confused with other possible uses of the word "enrichment," such as enrichment by removing the liquid component of a sample to concentrate the microorganism contained therein, or other forms of enrichment that do not include traditional facilitation of microorganism propagation. Culturing for enrichment for very short periods of time may be employed in some embodiments of methods described herein, but is not necessary and is for a much shorter period of time than traditional culturing for enrichment, if it is used at all.

As used herein "recombinant" refers to genetic (i.e., nucleic acid) modifications as usually performed in a laboratory to bring together genetic material that would not otherwise be found. This term is used interchangeably with the term "modified" herein.

As used herein "RLU" refers to relative light units as measured by a luminometer (e.g., GLOMAX® 96) or similar instrument that detects light. For example, the detection of the reaction between luciferase and an imidazopyrazinone substrate (furimazine) substrate (e.g., NANOLUC® with NANO-GLO®) is often reported in RLU detected.

As used herein "time to results" refers to the total amount of time from beginning of sample incubation to generated result. Time to results does not include any confirmatory testing time. Data collection can be done at any time after a result has been generated.

Samples

Each of the embodiments of the methods and systems of the present disclosure can allow for the rapid detection and quantification of MRSA in a sample. For example, methods according to the present disclosure can be performed in a shortened time with superior results. Bacterial cells detectable by the present disclosure include, but are not limited to, a variety of strains of MRSA in vitro or from a nasal swab. Samples may be liquid, solid, or semi-solid. Samples may be swabs of a surface. In some embodiments, the sample may be a nasal swab to detect nasal colonization of MRSA. In some embodiments, samples may include bodily materials, e.g., tissue or nasal fluid. In some embodiments, the sample may be whole blood, plasma, serum, or combinations thereof.

In some embodiments, samples may be used directly in the detection methods of the present disclosure, without preparation, concentration, or dilution. For example, liquid samples, including but not limited to, nasal swabs, may be assayed directly. Samples may be diluted or suspended in solution, which may include, but is not limited to, a buffered solution or a bacterial culture medium. A sample that is a solid or semi-solid may be suspending in a liquid by mincing, mixing or macerating the solid in the liquid. A sample should be maintained within a pH range that promotes bacteriophage attachment to the host bacterial cell. Preferably, a sample is maintained at a temperature that maintains the viability of any pathogen cells contained within the sample.

In some embodiments of the detection assay, the sample is maintained at a temperature that maintains the viability of any pathogen cell present in the sample. For example, during steps in which bacteriophages are attaching to bacterial cells, it is preferable to maintain the sample at a temperature that facilitates bacteriophage attachment. During steps in which bacteriophages are replicating within an infected bacterial cell or lysing such an infected cell, it is preferable to maintain the sample at a temperature that promotes bacteriophage replication and lysis of the host. Such temperatures are at least about 25° Celsius (C), more preferably no greater than about 45° C., most preferably about 37° C.

In some embodiments, an assay may include a selective agent. A selective agent may be added to the assay to inhibit or promote the growth of a microorganism, such as selective and non-selective antimicrobial agents that may inhibit or arrest microorganism growth, modulating agents (i.e., agents that may alter microorganism growth but are not considered antimicrobial agents), or enrichment agents (e.g., substances that may be required for auxotrophic microorganisms, such as hemin, or substances that may be required by fastidious organisms) or other components that may encourage microorganism growth. In some embodiments, the selective agent is an antimicrobial agent comprising, for example, cefoxitin.

Assays may include various appropriate control samples. For example, control samples containing no bacteriophage or control samples containing bacteriophage without bacteria may be assayed as controls for background signal levels.

Bacteriophage

As described in more detail herein, the compositions, methods, systems and kits of the present disclosure may comprise infectious agents for use in detection MRSA. In certain embodiments, the present disclosure provides a recombinant indicator bacteriophage, wherein the bacteriophage genome is genetically modified to include an indicator or reporter gene. In some embodiments, a composition may comprise a recombinant bacteriophage having an indicator gene incorporated into the genome of the bacteriophage.

Compositions of the present disclosure may comprise one or more genetically modified infectious agents (e.g., bacteriophages) and one or more indicator genes. In some embodiments, compositions can include cocktails of different indicator phages that may encode and express the same or different indicator proteins. In some embodiments, the cocktail of bacteriophage comprises at least two different types of recombinant bacteriophages derived from bacteriophage that are specific to *Staphylococcus aureus*.

A recombinant indicator bacteriophage can include a reporter or indicator gene. In certain embodiments of the infectious agent, expression of the indicator gene during bacteriophage replication following infection of a host bacterium results in a soluble indicator protein product. In certain embodiments, the indicator gene may be inserted into a late gene region of the bacteriophage. Late genes are generally expressed at higher levels than other phage genes, as they code for structural proteins. In some embodiments, an indicator bacteriophage is derived from a bacteriophage specific to *Staphylococcus aureus*.

Moreover, phage genes thought to be nonessential may have unrecognized function. For example, an apparently nonessential gene may have an important function in elevating burst size such as subtle cutting, fitting, or trimming functions in assembly. Therefore, deleting genes to insert an indicator may be detrimental. Most phages can package DNA that is a few percent larger than their natural genome. With this consideration, a smaller indicator gene may be a more appropriate choice for modifying a bacteriophage, especially one with a smaller genome. OpLuc and NANO-LUC® proteins are only about 20 kDa (approximately 500-600 bp to encode), while FLuc is about 62 kDa (approximately 1,700 bp to encode). Moreover, the reporter gene should not be expressed endogenously by the bacteria (i.e., is not part of the bacterial genome), should generate a high signal to background ratio, and should be readily detectable in a timely manner. Promega's NANOLUC® is a modified *Oplophorus gracihrostris* (deep sea shrimp) luciferase. In some embodiments, NANOLUC® (a luciferase) combined with Promega's NANO-GLO®, an imidazopyrazinone substrate (furimazine), can provide a robust signal with low background.

An indicator gene may express a variety of biomolecules. The indicator gene is a gene that expresses a detectable product or an enzyme that produces a detectable product. For example, in one embodiment the indicator gene encodes a luciferase enzyme. Various types of luciferase may be used. In alternate embodiments, and as described in more detail herein, the luciferase is one of *Oplophorus* luciferase, Firefly luciferase, Lucia luciferase, *Renilla* luciferase, or an engineered luciferase. In some embodiments, the luciferase gene is derived from *Oplophorus*. In some embodiments, the indicator gene is a genetically modified luciferase gene, such as NANOLUC®.

Thus, in some embodiments, the present disclosure provides a genetically modified bacteriophage comprising a non-bacteriophage indicator gene in the late (class III) gene region. In some embodiments, the non-native indicator gene is under the control of a late promoter. Using a viral late gene promoter insures the reporter gene (e.g., luciferase) is not only expressed at high levels, like viral capsid proteins, but also does not shut down like endogenous bacterial genes or even early viral genes.

Genetic modifications to infectious agents may include insertions, deletions, or substitutions of a small fragment of nucleic acid, a substantial part of a gene, or an entire gene. In some embodiments, inserted or substituted nucleic acids comprise non-native sequences. A non-native indicator gene may be inserted into a bacteriophage genome such that it is under the control of a bacteriophage promoter. Thus, in some embodiments, the non-native indicator gene is not part of a fusion protein. In some embodiments, the indicator protein product is soluble. In some embodiments, the present disclosure provides a method for detecting a bacterium of interest (e.g., *Staphylococcus aureus*) comprising the step of incubating a test sample with such a recombinant bacteriophage.

In some embodiments, expression of the indicator gene in progeny bacteriophage following infection of host bacteria results in a free, soluble protein product. In some embodiments, the non-native indicator gene is not contiguous with a gene encoding a structural phage protein and therefore does not yield a fusion protein. In some embodiments, the indicator or reporter is ideally free of the bacteriophage structure. That is, the indicator or reporter is not attached to the phage structure. As such, the gene for the indicator or reporter is not fused with other genes in the recombinant phage genome. This may greatly increase the sensitivity of the assay (down to a single bacterium), and simplify the assay, allowing the assay to be completed in two hours or less for some embodiments, as opposed to several hours due to additional purification steps required with constructs that produce detectable fusion proteins.

In some embodiments, the indicator phage encodes a reporter, such as a detectable enzyme. The indicator gene product may generate light and/or may be detectable by a color change. Various appropriate enzymes are commercially available, such as alkaline phosphatase (AP), horseradish peroxidase (HRP), or luciferase (Luc). In some embodiments, these enzymes may serve as the indicator moiety. In some embodiments, Firefly luciferase is the indicator moiety. In some embodiments, *Oplophorus* luciferase is the indicator moiety. In some embodiments, NANO-LUC® (a luciferase) is the indicator moiety. Other engineered luciferases or other enzymes that generate detectable signals may also be appropriate indicator moieties.

In some embodiments the preparation of the recombinant bacteriophage stock includes purification steps sufficient to remove substantially all of the residual indicator protein that may be associated with the bacteriophage, prior to use in a bacterial detection assay. As such the resulting preparation of parental recombinant bacteriophage, which is used to infect any target bacteria in the sample of interest, is substantially free of indicator protein.

Methods of Using Infectious Agents for Detecting MRSA

As noted herein, in certain embodiments, the present disclosure provides methods of using infectious bacteriophage for detecting MRSA. The methods of the present disclosure may be embodied in a variety of ways.

In some embodiments, the present disclosure provides a method for detecting MRSA from a sample (e.g., from a nasal swab) comprising the steps of: obtaining a sample, incubating the sample in an assay comprising a selective agent and one or more bacteriophage that infects *Staphylococcus aureus*, wherein the bacteriophage comprises an indicator gene such that expression of the indicator gene during bacteriophage replication following infection of the bacterium of interest results in production of a soluble indicator protein product; and detecting the indicator protein product, wherein positive detection of the indicator protein product indicates that MRSA is present in the sample. In some embodiments, the selective agent is an antibiotic comprising cefoxitin.

In some embodiments, the method includes capturing the indicator protein product for detection. The step of capturing the indicator protein product on a surface improves detection of a variety of MRSA strains at concentrations that generate very low numbers of colony-forming units. The indicator protein product can be contacted with a surface to capture the indicator protein product on the surface. For example, the indicator protein product may adhere or bind to the surface during the capture step. In some embodiments, the surface may include a microtiter plate, latex particle, lateral flow strip, bead, magnetic particle, dipstick, among others.

In some embodiments, the surface may comprise an immobilized binding partner. For example, one or more specific recognition elements can be immobilized in discrete areas of a surface in order to generate an array for analyte recognition. The indicator protein product can be brought into contact with the surface comprising the immobilized binding partner. In some embodiments, several different binding partners can be immobilized simultaneously on one surface. In some embodiments, the immobilized binding partner is an antibody or a fragment thereof.

In some embodiments, one or more different immobilized binding partners can be deposited (e.g., pipetted) on a surface (e.g., a plate) for capturing the indicator protein product. In some aspects, the surface can improve accessibility and capture of the indicator protein product by orienting immobilized binding partners. For example, an antibody can be deposited on a plate and incubated for a period of time. In some embodiments, the antibody can be rabbit or antibodies goat antibodies. Optionally, the plate can be washed after incubation. Subsequently, a NANOLUC® antibody can deposited on the coated plated. In some aspects, it is advantageous if the amount of the indicator protein product to be deposited on a surface with an immobilized binding partner is equal to or less than the amount of immobilized binding partner for the formation of a monolayer on the surface as a solid support. For example, the immobilized binding partner can be antibodies that are bound to a layer on the surface of a solid support, resulting in accessibility of their specific binding epitopes.

In some embodiments, the methods of the disclosure may comprise various other steps to increase sensitivity. The sensitivity of the method of detecting MRSA may be increased by one or more washing steps. For example, the method may comprise a step for washing the captured indicator protein product to remove excess bacteriophage and/or luciferase or other indicator protein contaminating the bacteriophage preparation. Additionally, captured microorganisms may be washed following incubation with antibiotic and the infectious agent, prior to addition of lysis buffer and substrate. These additional washing steps aid in the removal of excess parental phage and/or luciferase or other indicator protein contaminating the phage preparation. In some embodiments, a microorganism can be captured, washed, and then infected with the bacteriophage.

In some embodiments, the method includes adding a protein to the antibodies to promote infection by bacteriophage. S. aureus binds antibodies (e.g., IgG) in the blood preventing bacteriophage from infecting the cells. In some embodiments, Protein A is added to bind the antibodies in the blood thereby preventing the antibodies from binding to Staphylococcal aureus. When S. aureus cells divide in the presence of Protein A, the antibodies cannot bind to the daughter cells, allowing infection of the cells in the blood by the bacteriophage. In some embodiments, Protein A is added to a phage cocktail. For example, Protein A can be mixed with the phage cocktail prior to infection.

In certain embodiments, the assay may be performed to utilize a general concept that can be modified to accommodate different sample types or sizes and assay formats. Embodiments employing recombinant bacteriophage (i.e., indicator bacteriophage) may allow rapid detection of MRSA, with total assay times under 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12, 12.5, 13.0, 13.5, 14.0, 14.5, 15.0, 15.5, 16.0, 16.5, 17.0, 17.5, 18.0, 18.5, 19.0, 19.5, 20.0, 21.0, 21.5

22.0, 22.5, 23.0, 23.5, 24.0, 24.5 25.0, 25.5, or 26.0 hours, depending on the sample type, sample size, and assay format. For example, the amount of time required may be somewhat shorter or longer depending on the strain of bacteriophage and the strain of bacteria to be detected in the assay, type and size of the sample to be tested, conditions required for viability of the target, complexity of the physical/chemical environment, and the concentration of "endogenous" non-target bacterial contaminants.

EXAMPLES

Results depicted in the following examples demonstrate the effectiveness of the compositions, methods, and systems described herein for detecting MRSA from nasal swab specimens in a shortened time to results. The examples evaluated a novel bacteriophage-based assay used in diagnostic screening methods and systems described herein. This assay is a member of a new generation of luciferase-phage reporter systems utilizing NANOLUC® (a luciferase) to detect target species. The method proved to be highly inclusive and, when combined with cefoxitin selection, discriminated against the majority of non-resistant strains. Moreover, the method was capable of identifying low burdens of MRSA in nasal samples with little or no evidence of problematic interference. Ultimately, the data shows that this diagnostic screen may be a promising new tool for the detection of MRSA colonization from nasal swab specimens.

Materials and Methods

Bacterial Strains

Bacterial strains were obtained from the American Type Culture Collection (ATCC, Manassas, VA, USA) with the following exceptions. Salmonella enteritidis S492 was obtained from the University of Georgia Research Foundation and Staphylococcus aureus RN4220 was obtained from the University of Iowa. Clinical strains of Staphylococcus aureus were internally sourced from clinical microbiology labs (Laboratory Corporation of America Holdings). MRSA isolates from de-identified human clinical specimens originated from three geographically distinct USA sites (Burlington NC, Phoenix AZ, and Raritan NJ). MSSA isolates were obtained in a similar manner from one site (Burlington, NC). Determination of MRSA or MSSA was confirmed by plating on a selective chromogenic agar, MRSA Select II (Bio-Rad, Marnes-la-coquette, France). Strains were routinely grown at 37° C. in brain heart infusion (BHI) broth (Becton Dickinson and Company, Sparks, MD, USA) with shaking at 250 revolutions per minute (RPM).

Bacteriophage Source and Preparation of Stock

The assay includes two modified Staphylococcal aureus bacteriophage, MP115 and ISP. The Staphylococcal aureus bacteriophage are members of the Myoviridae family which includes large lytic Staphylococcal aureus bacteriophage. The MP115 bacteriophage was obtained from the Colorado School of Mines and the ISP bacteriophage was obtained from Emory University.

Stocks of bacteriophage were manufactured as follows. For MP115, overnight cultures of RN4220 were diluted, grown to exponential phase, and then infected at a multiplicity of infection (MOI) of 0.01. Cultures were monitored for loss of optical density (OD) as confirmation of viral propagation. Bacteriophage lysates were sub-sequentially clarified by 4° C. centrifugation at 10,000 rpm for 10 minutes. Clarified supernatants were centrifuged again at 4° C. and 10,000 rpm for two hours. Pellets were resuspended overnight in 1× TMS (50 mM Tris-HCL, 10 mM MgCl$_2$, and 300 mM NaCl). The bacteriophage preparation was then treated with 10 μg/mL DNase I and 5 μg/mL RNase. After treatment, the preparation was centrifuged at 5,000 rpm for 10 minutes at 4° C. The supernatant was removed and further purified by cesium chloride density gradient centrifugation (densities of 1.2, 1.3, 1.4, and 1.6) at 30,000 rpm for 2 hours at 20° C. The band containing phage was removed and the preparation placed in dialysis tubing (Spectra/Por 4, MWCO 12,000 to 14,000). Dialysis was performed in TMS with 2.4M NaCl for one hour, repeated in TMS with 0.9M NaCl, and repeated again in TMS with 0.3M NaCl.

For ISP, a similar procedure was used with the following exceptions: strain 12600 was used as a host, exponential cultures were infected at an MOI of 0.05, and an additional centrifugation at 5,000 rpm for 10 minutes at 4° C. was performed after overnight pellet resuspension, prior to treatment with DNase and RNase. Stock titers were determined by standard methods using plaque counting performed on host strains grown in semi-solid agar.

Engineering of Luciferase Reporter Phage

Target bacteriophage were transformed with a homologous recombination donor construct designed with a host-specific promoter and codon-optimized NANOLUC® (a luciferase) placed between two 500 bp flanking sequences with homology corresponding to suspected late gene regions in ISP. This construct was inserted into the PstI site of pBAVIKT5gfp (accession HQ191434). The host-specific promoter was modeled after previous studies. Cloning and codon optimization of NANOLUC® (a luciferase) was performed by Genewiz (South Plainfield, N.J., USA). This donor construct was utilized for both ISP and MP115 engineering, as the regions of homology share 99.9% identity.

Electroporation-competent *Staphylococcus aureus* were made from RN4220. To achieve this, overnight cultures of RN4220 were diluted and grown to mid-log phase in TryptoneSoya Broth (TSB) (Oxiod, Hampshire, United Kingdom). Bacteria were then chilled on ice for one hour, centrifuged at 4,000 g for 10 minutes at 4° C., and washed three times with ice-cold sterile deionized water. Following the washes, the final pellet was suspended in ice-cold 10% glycerol and prepared as an aliquot for −80° C. storage. Then, 100 ng of donor construct plasmid DNA was added to thawed aliquots and incubated for 30 minutes at room temperature prior to electroporation. Electroporation was performed using a MicroPulser Plus (1.8 kV voltage, 1 pulse, 2.5 msec time constant) with 0.2 cm cuvettes (Bio-Rad, Marnes-la-coquette, France). Cells were recovered in a B2 medium (10 g/L peptone, 25 g/L yeast extract, 25 g/L NaCl, 1 g/L K2HPO4, pH 7.5) and spread on TSB agar with 50 μg/mL kanamycin (Sigma, St. Louis, Mo., USA). Transformants were isolated and confirmed by expression of NANOLUC® (a luciferase). Colonies were grown for three hours in TSB with kanamycin before being tested. A mixture of 10 μL of culture, 50 μL of NANO-GLO® (an imidazopyrazinone substrate furimazine)) buffer, 15 μL *Renilla lysis* buffer, and 1 μL of NANO-GLO® substrate (an imidazopyrazinone substrate (furimazine)) (Promega, Madison, Wis., USA) was prepared and analyzed using a GLOMAX® Navigator (luminometer) (Promega, Madison, Wis., USA).

NANOLUC® (a luciferase)-positive cultures of transformed RN4220 were grown to early log-phase and infected with either MP115 or ISP at a MOI of 0.1 and incubated for three hours at 37° C. with shaking at 225 rpm. The phage lysate was centrifuged to remove cell debris, filtered through a 0.45 μM Whatman Puradisc filter (GE Health, Pittsburgh, Pa., USA), and finally buffer-exchanged into TMS using a 100K MWCO protein concentrator (Pierce). Limiting dilution enrichment was then performed to increase the frequency of recombinants prior to isolation by plaque screening on semi-solid agar. Individual plaques were isolated using a sterile pipet tip and mixed with 100 μL of TMS buffer. 10 μL of this suspension was used to infect 100 μL of strain 12600 in TSB for two hours at 37° C. After infection, 50 μL of NANO-GLO® (an imidazopyrazinone substrate (furimazine)) buffer, 15 μL *Renilla lysis* buffer, and 1 μL of NANO-GLO® substrate (an imidazopyrazinone substrate (furimazine)) was added to each well, before being assessed on a GLOMAX® Navigator (luminometer). Positive wells with high signal were filtered, diluted, and used to infect the next passage. This was repeated until three successive passages yielded plaques that were 100% positive and considered pure.

In Vitro Phage Detection Assays—Sensitivity, Inclusivity, and MSSA Exclusivity Overnight cultures were diluted in brain heart infusion (BHI) broth and 135 μL of the cultures diluted in BHI were transferred to two wells of a 96-well strip plate (Griener Bio-One GmbH, Frickenhausen, Germany) to obtain a desired colony forming unit (CFU) per well (e.g., 10, 1000 or 1000 CFU). An additional two wells consisting of only 135 μL of BHI broth were utilized to determine the medium background. One well for each sample served as a control well, and received 15 μL of BHI broth. The other well served as a selective well, and received 15 μL of BHI broth containing 22 μg/mL cefoxitin (Alfa Aesar, Ward Hill, MA, USA). The selective well had a final concentration of 2.2 μg/mL cefoxitin. When indicated, actual CFU for each sample was confirmed by plate counting on BHI agar. The 96-well strip plate was sealed with cover film (Thermo Fisher Scientific, Rochester, NY, USA) and incubated for four hours at 37° C. to facilitate enrichment and selection. A phage cocktail was prepared in a lysogeny broth (LB) (Gibco, Grand Island, NY, USA) and contained both engineered phages at 1.6×10$^8$ plaque forming units (PFU) per mL each. 10 μL of the phage cocktail was added to each well and mixed by pipetting before being covered once again with film. The plate was incubated for four hours at 37° C. to promote phage infection and production of luciferase in the presence of MRSA. A 65 μL of detection solution consisting of 50 μL NanoGlo Buffer, 15 μL *Renilla lysis* buffer, and 1 μL of NanoGlo substrate was added to each well and mixed by pipetting. Samples were read using a GloMax Navigator with a three-minute wait time and one-second integration. Results were evaluated with a cut-off of 600 relative light units (RLU), which is approximately three times the background observed with the medium alone.

In Vitro Phage Detection
Assays—Non-*Staphylococcus aureus* Exclusivity
and Bacterial Interference Overnight cultures of competitor organisms were diluted in BHI broth and 125 μL of the diluted cultures were transferred to four wells of a 96-well strip plate to obtain a desired CFU per well (e.g., 10, 1000 or 1000 CFU). An additional four wells consisting of only 125 μL of BHI broth were utilized to determine the medium background and baseline signal of MRSA (BAA-1720). Two wells of each sample were assigned to exclusivity tests, while the other two wells were used to assess bacterial interference. For exclusivity, 10 μL of BHI broth was added to both wells while 10 μL of BHI broth containing MRSA was added to bacterial interference wells. For each condition, one well served as a control well and received an additional 15 μL of BHI broth while the other served as a selective well and received 15 μL of BHI broth containing 22 μg/mL cefoxitin. Enrichment, phage infection, and CFU were then determined as previously described above.

Nasal Swab Phage Detection—Endogenous
Samples, MRSA Spike, and Autoluminescence

The BBL CultureSwab Liquid Stuart Double swab (Becton Dickinson and Company, Sparks, MD, USA) was used in the experiments described herein. Rayon nasal swabs were self-collected from volunteers who were instructed to insert the swab into one nostril, rotate at least five times, and repeat with the same swab in the second nostril. Prior to processing, specimens were stored overnight at 4° C. To evaluate endogenous nasal samples, one swab was eluted by vortexing for 15 seconds in 1 mL of BHI broth. 135 μL of this nasal elutant was added to two wells of a 96-well strip plate. These wells were assessed in the same manner as the 135 diluted cultures described above.

A reference method using both direct plating and enriched culture was employed to identify true MRSA colonization. For direct plating, 135 μL of nasal elutants used in the screen was plated on MRSA Select II agar. For the enriched culture method, one swab was placed in 3 mL of TSB with 6.5% NaCl (Fisher Scientific, Geel, Belgium) and grown overnight at 37° C. with shaking at 250 rpm. The next day, the culture was streaked on MRSA Select II agar. In both cases, manufacturer's instructions were followed to identify the presence or absence of MRSA colonization. Swabs were considered MRSA positive if either method (direct plating or enriched culture) yielded a positive result on selective agar.

The capacity for MRSA detection in a nasal matrix was assessed by spiking diluted cultures of MRSA into nasal elutants. To this end, 125 μL of nasal elutants was added to two wells of a 96-well strip plate for each sample. Both wells received 10 μL of a diluted MRSA culture. 40 unique nasal samples were assessed with eight samples assigned per MRSA strain tested (BAA-1707, BAA-1717, BAA-1720, BAA-1763, BAA-1766). As a control, 10 μL of each MRSA strain was also spiked into 125 μL of BHI broth. After spiking, the two wells were assessed in the same manner as the 135 μL diluted cultures as described above.

Autoluminescence of each nasal sample was assessed by mixing each sample with detection solution without the source of luciferase (phage cocktail). To accomplish this, 135 μL of each nasal elutant was combined with 25 μL of BHI broth in a 96-well strip plate. 65 μL of detection solution was then added to each well and pipetted to mix. The plate was read on a luminometer.

Example 1. Sensitivity and Inclusivity Studies

The methods and systems described herein are capable of identifying MRSA strains from diverse genetic backgrounds (Table 1). As shown in Table 1, inclusivity strains of MRSA were obtained from academic sources. For the vast majority of strains, detection of a variety of MRSA strains could be achieved at 100 CFU or less. This limit of detection and analytical sensitivity is similar to previously described PCR-based screens.

The bacteriophage-based MRSA screen comprised four hours of enrichment, two hours of infection, and subsequent detection of emitted light on a luminometer. Two wells of a 96-well strip plate were run for each sample consisting of one control well and one selective well. The selective well is used for MRSA determination and contains a MRSA selective agent, cefoxitin, while the control well contains only a bacterial culture medium and primarily gauges phage performance during assay development. Cefoxitin was shown to be a superior choice for phenotypic identification of MRSA in disc diffusion and agar dilution assay. The samples were enriched in these wells for four hours, which facilitated recovery, growth, and selection of resistant bacteria. Following this, a two-hour infection period with recombinant luciferase-encoding bacteriophage was performed. Production of luciferase, indicative of successful viral infection, is measured by detection of emitted light with a luminometer after the addition of substrate. 17 diverse MRSA strains were evaluated using this method at a starting target of 10, 100, or 1,000 colony forming units (CFU) in triplicate wells (Table 1). The values for CFU (determined from plate counts) and relative light units (RLU) are provided in Table S1. A positive result was determined based upon a cutoff of 600 RLU. This cutoff is approximately three times the background observed with culture media alone.

A positive result was obtained for 51 of 51 wells tested (100%) at both 100 CFU and 1,000 CFU per well in control conditions. At 10 CFU per well, 48 of 51 wells (94.1%) were positive. Three unique strains of MRSA were positive in only two of three wells at 10 CFU. These results highlight the ability of the phage cocktail to recognize diverse MRSA isolates. When cefoxitin was included for MRSA determination, a positive signal could still be detected for 51 of 51 wells (100%) at 1,000 CFU per well and 48 of 51 wells (94.1%) at 100 CFU per well. The inability to detect BAA-42, also known as HDE288, at 100 CFU under selection is not entirely unexpected. This strain belongs to an "archaic clone" of MRSA, associated with low-level and heterogeneous methicillin resistance. As shown in Table 1, 44 of 51 selective wells (86.3%) remained positive with only 10 CFU. A limit of detection was determined for each strain based upon the lowest CFU with 100% detection in both control and selective wells. 13 of the 17 MRSA strains tested could be reliably detected at 10 CFU per well, while three required 100 CFU per well. BAA-42 was the only strain to require greater than 100 CFU per well for consistent positive detection with MRSA selection. As shown in Table 1, the MRSA Assay demonstrates 100% inclusivity with the 17 MRSA strains tested at 100 CFU. The MRSA Assay also demonstrates selectivity for 48 of 51 MRSA strains tested. Overall, these results demonstrate the ability of this screen to detect the presence of genetically diverse MRSA strains at low bacterial burdens.

TABLE 1

| | | | | Inclusivity Strains of MRSA | | | | | | |
| | | | # of Positive[3] Control | | | # of Positive[3] Selective | | | LoD[4] |
| No. | Strain ID[1] | SCCmec[2] | PFGE[2] | 10 | 100 | 1000 | 10 | 100 | 1000 | CFU |
|---|---|---|---|---|---|---|---|---|---|---|
| 1 | BAA-44 | I | Iberian | 3/3 | 3/3 | 3/3 | 3/3 | 3/3 | 3/3 | 10 |
| 2 | BAA-41 | II | USA 100 | 2/3 | 3/3 | 3/3 | 3/3 | 3/3 | 3/3 | 100 |
| 3 | BAA-1761 | II | USA 100 | 3/3 | 3/3 | 3/3 | 3/3 | 3/3 | 3/3 | 10 |
| 4 | BAA-1720 | II | USA 200 | 3/3 | 3/3 | 3/3 | 3/3 | 3/3 | 3/3 | 10 |
| 5 | 33592 | III | ST239 | 3/3 | 3/3 | 3/3 | 3/3 | 3/3 | 3/3 | 10 |
| 6 | BAA-1717 | IV | USA 300 | 3/3 | 3/3 | 3/3 | 3/3 | 3/3 | 3/3 | 10 |
| 7 | BAA-1683 | IV | USA 400 | 3/3 | 3/3 | 3/3 | 3/3 | 3/3 | 3/3 | 10 |
| 8 | BAA-1707 | IV | USA 400 | 2/3 | 3/3 | 3/3 | 0/3 | 3/3 | 3/3 | 100 |
| 9 | BAA-1763 | IV | USA 500 | 3/3 | 3/3 | 3/3 | 3/3 | 3/3 | 3/3 | 10 |
| 9 | BAA-1754 | IV | USA 600 | 3/3 | 3/3 | 3/3 | 3/3 | 3/3 | 3/3 | 10 |
| 10 | BAA-1768 | IV | USA 800 | 3/3 | 3/3 | 3/3 | 2/3 | 3/3 | 3/3 | 100 |
| 11 | BAA-1747 | IV | USA 1000 | 3/3 | 3/3 | 3/3 | 3/3 | 3/3 | 3/3 | 10 |
| 12 | BAA-1764 | IV | USA 1100 | 3/3 | 3/3 | 3/3 | 3/3 | 3/3 | 3/3 | 10 |
| 14 | BAA-1766 | V | USA 700 | 3/3 | 3/3 | 3/3 | 3/3 | 3/3 | 3/3 | 10 |
| 15 | BAA-2094 | V | WA-MRSA | 3/3 | 3/3 | 3/3 | 3/3 | 3/3 | 3/3 | 10 |
| 16 | BAA-42 | VI | USA 800 | 2/3 | 3/3 | 3/3 | 0/3 | 0/3 | 3/3 | 1000 |
| 17 | BAA-2313 | XI | CC130 | 3/3 | 3/3 | 3/3 | 3/3 | 3/3 | 3/3 | 10 |
| | Total number of positives (%): | | | 48/51 | 51/51 | 51/51 | 44/51 | 48/51 | 51/51 | |
| | | | | (94.1) | (100) | (100) | (86.3) | (94.1) | (100) | |

[1]Strain ID corresponds to American Type Culture Collection (ATCC) catalog numbers.
[2]SCCmec Type and pulse field gel electrophoresis (PFGE) was available from the (ATCC).
[3]Positive wells were defined based on a signal cutoff of 600 relative light units (RLU).
[4]Limit of detection (LoD) was defined as the lowest colony forming units (CFU) that displayed 100% positive results across both control and selective wells.

TABLE S1

| | | | | CFU and RLU for in vitro sensitivity and inclusivity (Table 1) | | | | | |
| | | | Control RLU | | | Selective RLU | | | |
| Strain | Target CFU | CFU[1] | Well 1 | Well 2 | Well 3 | Well 1 | Well 2 | Well 3 | |
|---|---|---|---|---|---|---|---|---|---|
| BAA-44 | 10 | 3 | 14110 | 66460 | 31470 | 18440 | 56720 | 25170 | |
| BAA-44 | 100 | 28 | 476000 | 611800 | 683000 | 476900 | 492800 | 603300 | |
| BAA-44 | 1000 | 280 | 9183000 | 9172000 | 7862000 | 5249000 | 5136000 | 4743000 | |
| BAA-41 | 10 | 5 | 3969 | 176 | 18070 | 7585 | 3113 | 9434 | |
| BAA-41 | 100 | 49 | 508600 | 612900 | 346200 | 113600 | 159700 | 159900 | |
| BAA-41 | 1000 | 529 | 14780000 | 15850000 | 17730000 | 5131000 | 5079000 | 5018000 | |
| BAA-1761 | 10 | 5 | 866 | 30140 | 49990 | 8856 | 2533 | 4631 | |
| BAA-1761 | 100 | 51 | 267900 | 333500 | 306500 | 33880 | 47440 | 60150 | |
| BAA-1761 | 1000 | 510 | 6356000 | 4524000 | 5751000 | 1000000 | 1143000 | 1010000 | |
| BAA-1720 | 10 | 7 | 83630 | 74490 | 108800 | 52380 | 49230 | 32800 | |
| BAA-1720 | 100 | 71 | 811100 | 963600 | 1126000 | 169100 | 238100 | 288100 | |
| 33592 | 10 | 11 | 5623 | 15710 | 6434 | 1418 | 2601 | 2513 | |
| 33592 | 100 | 112 | 86640 | 73700 | 63510 | 18660 | 18710 | 25040 | |
| 33592 | 1000 | 1115 | 828700 | 903400 | 866900 | 210800 | 193400 | 197000 | |
| BAA-1717 | 10 | 10 | 261500 | 240200 | 339200 | 43620 | 2636 | 51360 | |
| BAA-1717 | 100 | 98 | 4324000 | 4548000 | 3875000 | 729200 | 690700 | 664100 | |
| BAA-1717 | 1000 | 1022 | 32010000 | 30010000 | 33700000 | 9901000 | 9117000 | 11980000 | |
| BAA-1683 | 10 | 10 | 62430 | 204100 | 13640 | 100500 | 143500 | 86780 | |
| BAA-1683 | 100 | 101 | 1010000 | 1119000 | 1213000 | 1031000 | 831200 | 970100 | |
| BAA-1683 | 1000 | 1010 | 11710000 | 11380000 | 12080000 | 11840000 | 9533000 | 10220000 | |
| BAA-1707 | 10 | 3 | 158 | 505900 | 108200 | 166 | 166 | 156 | |
| BAA-1707 | 100 | 31 | 1738000 | 1349000 | 1459000 | 701000 | 942200 | 1476000 | |
| BAA-1707 | 1000 | 278 | 32470000 | 33450000 | 33850000 | 16860000 | 20560000 | 22670000 | |
| BAA-1763 | 10 | 7 | 9399 | 14320 | 13450 | 933 | 3832 | 4106 | |
| BAA-1763 | 100 | 68 | 250700 | 257700 | 206000 | 16340 | 37160 | 32910 | |
| BAA-1763 | 1000 | 67 | 1317000 | 1411000 | 1461000 | 289700 | 326600 | 304100 | |
| BAA-1754 | 10 | 14 | 335700 | 460500 | 404900 | 186800 | 251300 | 195400 | |
| BAA-1754 | 100 | 137 | 4676000 | 4059000 | 4630000 | 2619000 | 1824000 | 2948000 | |
| BAA-1754 | 1000 | 1249 | 39970000 | 43020000 | 45350000 | 23920000 | 23090000 | 23370000 | |
| BAA-1768 | 10 | 1 | 1101000 | 1038000 | 346000 | 4526 | 3589 | 172 | |
| BAA-1768 | 100 | 14 | 8948000 | 8918000 | 5671000 | 62360 | 53840 | 65240 | |
| BAA-1768 | 1000 | 135 | 62560000 | 71830000 | 69130000 | 1195000 | 1206000 | 913700 | |
| BAA-1747 | 10 | 11 | 21440 | 26280 | 33830 | 9141 | 15180 | 13110 | |
| BAA-1747 | 100 | 105 | 90310 | 138600 | 180700 | 88070 | 77420 | 80040 | |
| BAA-1747 | 1000 | 1050 | 676700 | 698800 | 757100 | 335500 | 387200 | 418900 | |
| BAA-1764 | 10 | 14 | 332500 | 267300 | 96030 | 169000 | 109000 | 109600 | |
| BAA-1764 | 100 | 137 | 2954000 | 3075000 | 2388000 | 1123000 | 1096000 | 1138000 | |
| BAA-1764 | 1000 | 1365 | 21630000 | 20130000 | 24990000 | 11590000 | 10320000 | 10430000 | |
| BAA-1766 | 10 | 6 | 90370 | 262800 | 200800 | 7756 | 9880 | 1067 | |

TABLE S1-continued

| | | | Control RLU | | | Selective RLU | | |
| --- | --- | --- | --- | --- | --- | --- | --- | --- |
| Strain | Target CFU | CFU[1] | Well 1 | Well 2 | Well 3 | Well 1 | Well 2 | Well 3 |
| BAA-1766 | 100 | 58 | 1641000 | 1763000 | 1984000 | 155500 | 95160 | 223400 |
| BAA-1766 | 1000 | 575 | 30650000 | 27920000 | 31810000 | 2236000 | 1752000 | 2099000 |
| BAA-2094 | 10 | 9 | 424200 | 545500 | 273900 | 127600 | 166500 | 117900 |
| BAA-2094 | 100 | 86 | 4371000 | 4259000 | 4753000 | 1274000 | 830900 | 1051000 |
| BAA-2094 | 1000 | 1172 | 42320000 | 45310000 | 40370000 | 9401000 | 9215000 | 10580000 |
| BAA-42 | 10 | 3 | 646 | 786 | 390 | 165 | 145 | 247 |
| BAA-42 | 100 | 30 | 5895 | 7651 | 6028 | 328 | 457 | 390 |
| BAA-42 | 1000 | 295 | 30870 | 42400 | 34910 | 3511 | 2770 | 4244 |
| BAA-2313 | 10 | 8 | 449000 | 323100 | 603700 | 39570 | 77110 | 16000 |
| BAA-2313 | 100 | 75 | 6515000 | 6700000 | 6655000 | 289200 | 192400 | 141400 |
| BAA-2313 | 1000 | 750 | 53120000 | 54760000 | 56490000 | 4115000 | 3926000 | 3840000 |
| BHI[2] | — | — | 148 | 126 | 162 | 115 | 141 | 152 |

[1]CFU were determined by plate counting (in duplicate) for samples with a target of 100 CFU and calculated from dilutions for samples with a target of 10 and 1000 CFU.
[2]BHI broth was used in place of bacterial culture to reveal assay background.

Example 2. Exclusivity and Specificity of MRSA Screen In Vitro

In addition to sensitive MRSA detection, a successful MRSA assay must also demonstrate the ability to exclude a majority of methicillin-sensitive *Staphylococcus aureus* (MSSA) strains. Table 2 shows five well-characterized strains of MSSA that were evaluated using the methods described herein at 100, 1,000, and 10,000 CFU in triplicate wells and provides the CFU value, determined from plate counts, and RLU values. The MRSA control wells did not include cefoxitin and the MRSA selective wells included cefoxitin. As expected, MSSA strains were positive in 100% of control wells at CFU levels of 100, 1,000, and 10,000. The inclusion of cefoxitin in the selective wells resulted in significant reduction of positive results. In the MRSA selective wells including cefoxitin, 0 of 15 (0%) selective wells were positive at 100 CFU, while only 1 of 15 (6.7%) selective wells were positive at 1,000 CFU and 10,000 CFU. These results support the ability of the MRSA assay to discriminate against most MSSA strains.

TABLE 2

| No. | Strain ID[1] | Type | # of Positive[2] Control | | | # of Positive[2] Selective Cefoxitin in Assay | | |
| --- | --- | --- | --- | --- | --- | --- | --- | --- |
| | | | 100 | 1000 | 10000 | 100 | 1000 | 10000 |
| 1 | 6538 | MSSA | 3/3 | 3/3 | 3/3 | 0/3 | 0/3 | 0/3 |
| 2 | 12600 | MSSA | 3/3 | 3/3 | 3/3 | 0/3 | 1/3 | 1/3 |
| 3 | 14775 | MSSA | 3/3 | 3/3 | 3/3 | 0/3 | 0/3 | 0/3 |
| 4 | 25923 | MSSA | 3/3 | 3/3 | 3/3 | 0/3 | 0/3 | 0/3 |
| 5 | 29213 | MSSA | 3/3 | 3/3 | 3/3 | 0/3 | 0/3 | 0/3 |
| | Total number of positives (%): | | 15/15 (100) | 15/15 (100) | 15/15 (100) | 0/15 (0.0) | 1/15 (6.7) | 1/15 (6.7) |

[1]Strain ID corresponds to American Type Culture Collection (ATCC) catalog numbers.
[2]Positive wells were defined based on a signal cutoff of 600 RLU.

TABLE S2

CFU and RLU for in vitro discrimination of MSSA (Table 2)

| Strain | Target CFU | CFU[1] | Control RLU | | | Selective RLU | | |
| --- | --- | --- | --- | --- | --- | --- | --- | --- |
| | | | Well 1 | Well 2 | Well 3 | Well 1 | Well 2 | Well 3 |
| 6538 | 100 | 43 | 847900 | 1997000 | 1008000 | 130 | 146 | 142 |
| 6538 | 1000 | 425 | 15860000 | 14890000 | 15170000 | 148 | 133 | 153 |
| 6538 | 10000 | 4250 | 151500000 | 153200000 | 158100000 | 183 | 195 | 223 |
| 12600 | 100 | 192 | 3399000 | 3173000 | 4102000 | 136 | 192 | 131 |
| 12600 | 1000 | 1920 | 43220000 | 39030000 | 38470000 | 155 | 775 | 143 |
| 12600 | 10000 | 19200 | 125700000 | 126800000 | 147500000 | 232 | 653 | 160 |
| 14775 | 100 | 166 | 5037000 | 5107000 | 5413000 | 140 | 142 | 151 |
| 14775 | 1000 | 1655 | 66210000 | 60400000 | 64720000 | 110 | 141 | 142 |
| 14775 | 10000 | 16550 | 97360000 | 95240000 | 96340000 | 123 | 131 | 150 |
| 25923 | 100 | 65 | 1977000 | 2553000 | 1673000 | 146 | 116 | 161 |
| 25923 | 1000 | 645 | 25380000 | 22220000 | 25040000 | 121 | 128 | 152 |
| 25923 | 10000 | 6450 | 58650000 | 60290000 | 65420000 | 125 | 143 | 157 |
| 29213 | 100 | 174 | 83090 | 103900 | 99960 | 121 | 130 | 131 |

TABLE S2-continued

| CFU and RLU for in vitro discrimination of MSSA (Table 2) | | | | | | | | |
|---|---|---|---|---|---|---|---|---|
| | | | Control RLU | | | Selective RLU | | |
| Strain | Target CFU | CFU[1] | Well 1 | Well 2 | Well 3 | Well 1 | Well 2 | Well 3 |
| 29213 | 1000 | 1740 | 308400 | 296400 | 273700 | 118 | 151 | 130 |
| 29213 | 10000 | 17400 | 700800 | 777800 | 784500 | 133 | 268 | 132 |
| BHI[2] | — | — | 181 | 115 | — | 125 | 111 | — |

[1]CFU were determined by plate counting (in duplicate) for samples with a target of 100 CFU per well and calculated from dilutions for samples with a target of 10 and 1000 CFU.
[2]BHI broth was used in place of bacterial culture to identify assay background.

As shown in Table 3, beyond MSSA, the exclusivity of the MRSA screen was evaluated in vitro against a panel of 40 strains, encompassing 21 unique genera and 32 distinct species. The values for CFU (determined from plate counts) and RLU are provided in Table S3. The CFU for each exclusivity strain was greater than 1,500 CFU per well (median CFU of 15,950). When assessing specificity, Table 3 shows that 6 of 40 (15%) strains were positive in the control well. The positive signal in this condition is the result of cross-reactivity of the phage cocktail and was observed with *Staphylococcus* and *Bacillus* species. Many *Staphylococcus aureus* phages have been demonstrated to be polyvalent, lysing both coagulase-positive and coagulase-negative *staphylococcal* species. Adsorption of *staphylococcal* phages by *Bacillus* species has previously been reported and may be associated with similarities in their cell wall teichoic acid (WTA). Despite this cross-reactivity, 0 of 40 strains were positive in the selective condition and would not have resulted in false positives for MRSA. These results demonstrate the specificity of the phage cocktail used in the experiments described herein and the exclusivity of the overall assay.

The ability of the MRSA screen to detect low numbers of MRSA in the presence of excess competitor burdens was assessed. To this end, approximately 50 CFU of MRSA was combined with at least a 20-fold excess of each strain from the exclusivity panel (Table 3). The values for CFU (determined from plate count) and RLU are provided in Table S3. Surprisingly, 39 of 40 (97.5%) and 40 of 40 (100%) wells were positive in the control and selective conditions, respectively, in the presence of competitor species. *Streptococcus pneumoniae* inhibited detection in the control conditions when tested at 100-fold excess. This is not surprising, given the known antagonism between these species both in vitro and in vivo. Critically, this effect was lost in the presence of cefoxitin (MRSA selective condition) and thus would not result in a false negative for MRSA. This data demonstrates the ability of this screen to detect low-levels of MRSA in environments containing excess competing organisms.

TABLE 3

| In vitro exclusivity and assay performance with bacterial competitors | | | | | | |
|---|---|---|---|---|---|---|
| | | | Exclusivity[3] (Competitor only) | | Bacterial Interference[4] (Competitor + MRSA) | |
| Genus | Species | Strain ID[1] | Control | Selective | Control | Selective |
| *Staphylococcus* | *epidermidis* | 14990 | Negative | Negative | Positive | Positive |
| | | 700583 | Positive | Negative | Positive | Positive |
| | *haemolyticus* | 29970 | Positive | Negative | Positive | Positive |
| | | 700564 | Negative | Negative | Positive | Positive |
| | *hominis* | 27844 | Negative | Negative | Positive | Positive |
| | *lugdunensis* | 49576 | Negative | Negative | Positive | Positive |
| | *saprophyticus* | 15305 | Positive | Negative | Positive | Positive |
| | *warneri* | 49454 | Positive | Negative | Positive | Positive |
| *Bacillus* | *licheniformis* | 9789 | Negative | Negative | Positive | Positive |
| | *pumilus* | 700814 | Positive | Negative | Positive | Positive |
| | *subtilis* | 6051 | Positive | Negative | Positive | Positive |
| *Citrobacter* | *braaki* | 51113 | Negative | Negative | Positive | Positive |
| | *freundii* | 8090 | Negative | Negative | Positive | Positive |
| | *koseri* | 25408 | Negative | Negative | Positive | Positive |
| *Enterococcus* | *faecalis* | 19433 | Negative | Negative | Positive | Positive |
| | *faecium* | 19434 | Negative | Negative | Positive | Positive |
| *Klebsiella* | *oxytoca* | 43165 | Negative | Negative | Positive | Positive |
| | *pneumoniae* | 4352 | Negative | Negative | Positive | Positive |
| *Listeria* | *innocua* | 51742 | Negative | Negative | Positive | Positive |
| | *ivanovii* | 19119 | Negative | Negative | Positive | Positive |
| | *monocytogenes* | 19115 | Negative | Negative | Positive | Positive |
| | *welshimeri* | 35897 | Negative | Negative | Positive | Positive |
| *Proteus* | *mirabilis* | 43071 | Negative | Negative | Positive | Positive |
| | *vulgaris* | 33420 | Negative | Negative | Positive | Positive |
| *Shigella* | *flexneri* | 12022 | Negative | Negative | Positive | Positive |
| | *sonnei* | 9290 | Negative | Negative | Positive | Positive |
| *Streptococcus* | *pneumoniae* | 6303 | Negative | Negative | Negative | Positive |
| | *pyogenes* | 12202 | Negative | Negative | Positive | Positive |
| *Acinetobacter* | *baumannii* | 19606 | Negative | Negative | Positive | Positive |
| *Edwardsiella* | *tarda* | 15947 | Negative | Negative | Positive | Positive |
| *Enterobacter* | *kobei* | BAA-260 | Negative | Negative | Positive | Positive |

TABLE 3-continued

In vitro exclusivity and assay performance with bacterial competitors

| Genus | Species | Strain ID[1] | Exclusivity[3] (Competitor only) | | Bacterial Interference[4] (Competitor + MRSA) | |
| | | | Control | Selective | Control | Selective |
| --- | --- | --- | --- | --- | --- | --- |
| *Escherichia* | *coli* | 25922 | Negative | Negative | Positive | Positive |
| *Hafnia* | *alvei* | 13337 | Negative | Negative | Positive | Positive |
| *Moraxella* | *catarrhalis* | 25238 | Negative | Negative | Positive | Positive |
| *Morganella* | *morganii* | 25830 | Negative | Negative | Positive | Positive |
| *Pluralibacter* | *gergoviae* | 33028 | Negative | Negative | Positive | Positive |
| *Pseudomonas* | *aeruginosa* | 27853 | Negative | Negative | Positive | Positive |
| *Salmonella* | *enteriditis* | S492 | Negative | Negative | Positive | Positive |
| *Serratia* | *marcescens* | 13880 | Negative | Negative | Positive | Positive |
| *Yersinia* | *enterocolitica* | 23715 | Negative | Negative | Positive | Positive |
| Total number of positives[2] (%): | | | 6/40 (15.0) | 0/40 (0.0) | 39/40 (97.5) | 40/40 (100) |

[1]Strain ID corresponds with ATCC catalog number for all strains except *Salmonella enteritidis* strain S492.
[2]Positive wells were defined based on a signal cutoff of 600 RLU.
[3]For exclusivity, each competitor strain was assessed alone at greater than 1,500 CFU per well.
[4]For bacterial interference, MRSA (BAA-1720) was added at approximately 50 CFU per well while indicated competitor strains were added in excess (at least 20-fold).

TABLE S3

CFU and RLU for exclusivity and assay performance with bacterial competitors (Table 3)

| Genus | Species | Strain ID | Competitor CFU[1] | RLU for Exclusivity[3] (Competitor only) | | RLU for Bacterial Interference[4] (Competitor + MRSA) | | |
| | | | | Control | Selective | MRSA CFU[1] | Control | Selective |
| --- | --- | --- | --- | --- | --- | --- | --- | --- |
| *Staphylococcus* | *epidermidis* | 14990 | 62300 | 256 | 152 | 52 | 199300 | 119800 |
| | | 700583 | 36600 | 317400 | 170 | 52 | 403700 | 166600 |
| | *haemolyticus* | 29970 | 14400 | 1759000 | 138 | 52 | 2447000 | 154000 |
| | | 700564 | 30000 | 176 | 223 | 52 | 182500 | 90610 |
| | *hominis* | 27844 | 9800 | 170 | 175 | 52 | 467100 | 190200 |
| | *lugdunensis* | 49576 | 16100 | 118 | 270 | 71 | 362300 | 90950 |
| | *saprophyticus* | 15305 | 16650 | 6282 | 250 | 52 | 420100 | 231500 |
| | *warneri* | 49454 | 9750 | 41750000 | 455 | 53 | 45850000 | 92070 |
| *Bacillus* | *licheniformis* | 9789 | 7750 | 78 | 133 | 53 | 313900 | 79960 |
| | *pumilus* | 700814 | 8200 | 62250 | 131 | 53 | 108500 | 81130 |
| | *subtilis* | 6051 | 4900 | 3173 | 151 | 66 | 68880 | 63050 |
| *Citrobacter* | *braaki* | 51113 | 14450 | 70 | 90 | 48 | 77660 | 28430 |
| | *freundii* | 8090 | 15350 | 136 | 138 | 52 | 202300 | 65670 |
| | *koseri* | 25408 | 28050 | 56 | 132 | 49 | 44640 | 36100 |
| *Enterococcus* | *faecalis* | 19433 | 32700 | 92 | 115 | 49 | 22490 | 10540 |
| | *faecium* | 19434 | 9150 | 147 | 132 | 52 | 447300 | 187500 |
| *Klebsiella* | *oxytoca* | 43165 | 15950 | 88 | 175 | 52 | 141900 | 97480 |
| | *pneumoniae* | 4352 | 56700 | 46 | 115 | 49 | 22100 | 249500 |
| *Listeria* | *innocua* | 51742 | 23100 | 121 | 110 | 49 | 299100 | 228900 |
| | *ivanovii* | 19119 | 82600 | 88 | 100 | 49 | 368400 | 110800 |
| | *monocytogenes* | 19115 | 33150 | 101 | 143 | 71 | 331400 | 114900 |
| | *welshimeri* | 35897 | 9400 | 156 | 112 | 48 | 253400 | 181100 |
| *Proteus* | *mirabilis* | 43071 | 7450 | 25 | 117 | 49 | 17090 | 279200 |
| | *vulgaris* | 33420 | 11600 | 27 | 96 | 49 | 29170 | 171800 |
| *Shigella* | *flexneri* | 12022 | 34500 | 78 | 101 | 52 | 30360 | 13950 |
| | *sonnei* | 9290 | 10900 | 65 | 140 | 48 | 29360 | 75300 |
| *Streptococcus* | *pneumoniae* | 6303 | 34000 | 75 | 143 | 53 | 178 | 24610 |
| | *pyogenes* | 12202 | 1500 | 142 | 116 | 64 | 193800 | 91370 |
| *Acinetobacter* | *baumannii* | 19606 | 16450 | 78 | 88 | 49 | 232500 | 113600 |
| *Edwardsiella* | *tarda* | 15947 | 20200 | 90 | 132 | 52 | 118200 | 84540 |
| *Enterobacter* | *kobei* | BAA-260 | 11250 | 118 | 97 | 49 | 455400 | 180300 |
| *Escherichia* | *coli* | 25922 | 8850 | 108 | 101 | 71 | 97980 | 46360 |
| *Hafnia* | *alvei* | 13337 | 14850 | 78 | 92 | 49 | 338500 | 198800 |
| *Moraxella* | *catarrhalis* | 25238 | 8350 | 130 | 115 | 53 | 315800 | 360300 |
| *Morganella* | *morganii* | 25830 | 30000 | 76 | 212 | 52 | 155900 | 145400 |
| *Pluralibacter* | *gergoviae* | 33028 | 17400 | 80 | 65 | 49 | 203400 | 78990 |
| *Pseudomonas* | *aeruginosa* | 27853 | 20500 | 138 | 142 | 52 | 175800 | 53400 |
| *Salmonella* | *enteritidis* | S492 | 19150 | 46 | 121 | 49 | 207900 | 314600 |
| *Serratia* | *marcescens* | 13880 | 15950 | 86 | 91 | 48 | 92500 | 26200 |
| *Yersinia* | *enterocolitica* | 23715 | 14250 | 102 | 112 | 71 | 334100 | 126200 |
| BHI[2] | — | — | — | 117 | 111 | 49 | 498000 | 171000 |

[1]CFU were determined by plate counting (in duplicate) of either diluted samples for competitors or directly for MRSA.
[2]BHI broth was used in place of bacterial culture to identify assay background.
[3]For exclusivity, each competitor strain was assessed alone at the indicated CFU per well.
[4]For bacterial interference, MRSA (BAA-1720) was added at the burden indicated in combination with the stated competitor CFU per well.

Example 3. Screen Performance Among Circulating *Staphylococcus aureus* Clinical Isolates in Vitro MRSA isolates from human clinical specimens were obtained internally from three geographically distinct clinical microbiology labs in the United States (Burlington NC, Phoenix AZ, and Raritan NJ). MSSA isolates were obtained in a similar fashion from one site (Burlington, NC). MRSA or MSSA identification was confirmed by plating on selective chromogenic agar. A total of 390 clinical MRSA strains were isolated from unique specimens and evaluated with the MRSA screen. RLU and CFU values for each strain are provided (Table S4).

Table 4 shows that the median burden of MRSA tested was 47 CFU per well. As shown in Table 4, 388 of 390 clinical MRSA strains (99.5%) were positively detected in the control well. Under cefoxitin selection, 381 of 390 (97.7%) clinical MRSA strains were positive and were identified by the screen as MRSA. Clinical MSSA strains were tested for exclusion at higher burdens, either 10- or 100-times MRSA levels (500 CFU and 5,000 CFU, respectively). 122 of 123 (99.2%) clinical MSSA strains were positively detected in the control condition of either inoculum. In selective wells, however, positive signal from 500 CFU dropped to 8 of 123 (6.5%) MSSA strains. At approximately 5,000 CFU per well, this rate of false positives increased to 21 of 123 (17.1%) strains. This suggests that, while most MSSA strains will be negative, some may overwhelm selection at high burdens and result in false positives. Critically, of 513 tested clinical *Staphylococcus aureus* isolates, 510 (99.4%) were positive in the control condition. This continues to support the notion that the phage cocktail utilized in the described methods and systems yields broad-host-range coverage. Overall, these results show the capability of this screen to successfully recognize and detect the vast majority of clinical MRSA strains, while excluding most clinical MSSA strains.

TABLE 4

Performance of MRSA screen with clinical *Staphylococcus Aureus*

| | Clinical MRSA | | | Clinical MSSA | | |
| | $CFU^2$ | Control | Selective | $CFU^3$ | Control | Selective |
|---|---|---|---|---|---|---|
| Number of positives[1] (%): | 50 | 388/390 (99.5) | 381/390 (97.7) | 500 | 122/123 (99.2) | 8/123 (6.5) |
| | | | | 5,000 | 122/123 (99.2) | 21/123 (17.1) |

[1]Positive wells were defined based on a signal cutoff of 600 RLU.
[2]The median CFU tested for clinical MRSA strains was 47 CFU per well. The burden for each strain can be found in the supplement.
[3]The median CFU per well tested for clinical MSSA was 850 CFU for "500" and 8,500 CFU for "5,000."

TABLE S4-continued

CFU and RLU for MRSA screen with clinical *Staphylococcus aureus* (Table 4)

| Strain ID | Source | Type | CFU | Control RLU | Selective RLU |
|---|---|---|---|---|---|
| BNC 010 | Burlington, NC | MRSA | 48 | 363600 | 1705 |
| BNC 011 | Burlington, NC | MRSA | 23 | 609700 | 412000 |
| BNC 012 | Burlington, NC | MRSA | 47 | 1377000 | 73580 |
| BNC 013 | Burlington, NC | MRSA | 63 | 182400 | 56490 |
| BNC 014 | Burlington, NC | MRSA | 47 | 1071000 | 134500 |
| BNC 015 | Burlington, NC | MRSA | 22 | 318700 | 80540 |
| BNC 016 | Burlington, NC | MRSA | 40 | 683200 | 103900 |
| BNC 017 | Burlington, NC | MRSA | 44 | 782800 | 123000 |
| BNC 018 | Burlington, NC | MRSA | 36 | 616200 | 137200 |
| BNC 019 | Burlington, NC | MRSA | 52 | 22610 | 24300 |
| BNC 020 | Burlington, NC | MRSA | 80 | 349000 | 162200 |
| BNC 021 | Burlington, NC | MRSA | 52 | 20110 | 577 |
| BNC 022 | Burlington, NC | MRSA | 47 | 168600 | 12950 |
| BNC 023 | Burlington, NC | MRSA | 40 | 230200 | 54760 |
| BNC 024 | Burlington, NC | MRSA | 46 | 4671 | 2631 |
| BNC 025 | Burlington, NC | MRSA | 76 | 1803000 | 251700 |
| BNC 026 | Burlington, NC | MRSA | 100 | 1185000 | 246500 |
| BNC 027 | Burlington, NC | MRSA | 33 | 1136000 | 103300 |
| BNC 028 | Burlington, NC | MRSA | 31 | 335300 | 156300 |
| BNC 030 | Burlington, NC | MRSA | 44 | 568800 | 62820 |
| BNC 031 | Burlington, NC | MRSA | 64 | 377200 | 14960 |
| BNC 032 | Burlington, NC | MRSA | 24 | 53640 | 21400 |
| BNC 033 | Burlington, NC | MRSA | 35 | 526500 | 84710 |
| BNC 034 | Burlington, NC | MRSA | 38 | 1018000 | 74260 |
| BNC 035 | Burlington, NC | MRSA | 42 | 861600 | 232900 |
| BNC 036 | Burlington, NC | MRSA | 41 | 1136000 | 3531 |
| BNC 037 | Burlington, NC | MRSA | 53 | 694700 | 229600 |
| BNC 038 | Burlington, NC | MRSA | 19 | 106300 | 70910 |
| BNC 039 | Burlington, NC | MRSA | 49 | 101200 | 34560 |
| BNC 040 | Burlington, NC | MRSA | 36 | 152200 | 34310 |
| BNC 042 | Burlington, NC | MRSA | 50 | 690900 | 155200 |
| BNC 043 | Burlington, NC | MRSA | 54 | 576300 | 49510 |
| BNC 044 | Burlington, NC | MRSA | 31 | 748800 | 26470 |
| BNC 045 | Burlington, NC | MRSA | 23 | 329000 | 50790 |
| BNC 046 | Burlington, NC | MRSA | 36 | 52100 | 26650 |
| BNC 047 | Burlington, NC | MRSA | 44 | 375200 | 71090 |
| BNC 048 | Burlington, NC | MRSA | 60 | 656100 | 200600 |

TABLE S4

CFU and RLU for MRSA screen with clinical *Staphylococcus aureus* (Table 4)

| Strain ID | Source | Type | CFU | Control RLU | Selective RLU |
|---|---|---|---|---|---|
| BNC 001 | Burlington, NC | MRSA | 52 | 479400 | 39000 |
| BNC 002 | Burlington, NC | MRSA | 77 | 407500 | 305000 |
| BNC 003 | Burlington, NC | MRSA | 84 | 588600 | 143300 |
| BNC 004 | Burlington, NC | MRSA | 63 | 183300 | 210100 |
| BNC 005 | Burlington, NC | MRSA | 38 | 358900 | 22610 |
| BNC 006 | Burlington, NC | MRSA | 33 | 18600 | 24580 |
| BNC 007 | Burlington, NC | MRSA | 19 | 190800 | 3708 |
| BNC 008 | Burlington, NC | MRSA | 36 | 86900 | 1905 |
| BNC 009 | Burlington, NC | MRSA | 41 | 522000 | 109200 |

TABLE S4-continued

CFU and RLU for MRSA screen with clinical *Staphylococcus aureus* (Table 4)

| Strain ID | Source | Type | CFU | Control RLU | Selective RLU |
|---|---|---|---|---|---|
| BNC 049 | Burlington, NC | MRSA | 51 | 138700 | 9575 |
| BNC 050 | Burlington, NC | MRSA | 44 | 326200 | 41580 |
| BNC 051 | Burlington, NC | MRSA | 37 | 423000 | 141200 |
| BNC 052 | Burlington, NC | MRSA | 56 | 713000 | 80260 |
| BNC 053 | Burlington, NC | MRSA | 73 | 1009000 | 384400 |
| BNC 054 | Burlington, NC | MRSA | 61 | 167200 | 72850 |
| BNC 055 | Burlington, NC | MRSA | 57 | 263400 | 247200 |
| BNC 056 | Burlington, NC | MRSA | 62 | 553400 | 83970 |
| BNC 057 | Burlington, NC | MRSA | 45 | 472600 | 4302 |

TABLE S4-continued

CFU and RLU for MRSA screen with clinical
*Staphylococcus aureus* (Table 4)

| Strain ID | Source | Type | CFU | Control RLU | Selective RLU |
|---|---|---|---|---|---|
| BNC 058 | Burlington, NC | MRSA | 68 | 341900 | 110600 |
| BNC 059 | Burlington, NC | MRSA | 19 | 57110 | 1343 |
| BNC 060 | Burlington, NC | MRSA | 54 | 517300 | 63320 |
| BNC 061 | Burlington, NC | MRSA | 58 | 844800 | 254000 |
| BNC 062 | Burlington, NC | MRSA | 92 | 120700 | 31180 |
| BNC 063 | Burlington, NC | MRSA | 37 | 158100 | 342100 |
| BNC 064 | Burlington, NC | MRSA | 27 | 68450 | 276100 |
| BNC 065 | Burlington, NC | MRSA | 41 | 266300 | 56820 |
| BNC 066 | Burlington, NC | MRSA | 54 | 142700 | 14340 |
| BNC 067 | Burlington, NC | MRSA | 53 | 220100 | 343 |
| BNC 068 | Burlington, NC | MRSA | 28 | 444500 | 37440 |
| BNC 069 | Burlington, NC | MRSA | 20 | 84730 | 148000 |
| BNC 070 | Burlington, NC | MRSA | 44 | 527700 | 62200 |
| BNC 071 | Burlington, NC | MRSA | 20 | 314400 | 27510 |
| BNC 072 | Burlington, NC | MRSA | 16 | 1711000 | 69730 |
| BNC 073 | Burlington, NC | MRSA | 58 | 753800 | 395500 |
| BNC 074 | Burlington, NC | MRSA | 47 | 749100 | 277700 |
| BNC 075 | Burlington, NC | MRSA | 34 | 487300 | 379200 |
| BNC 076 | Burlington, NC | MRSA | 56 | 1207000 | 213200 |
| BNC 077 | Burlington, NC | MRSA | 21 | 407800 | 107200 |
| BNC 078 | Burlington, NC | MRSA | 28 | 1453000 | 256600 |
| BNC 079 | Burlington, NC | MRSA | 37 | 278600 | 79120 |
| BNC 080 | Burlington, NC | MRSA | 30 | 1149000 | 278800 |
| BNC 081 | Burlington, NC | MRSA | 34 | 739700 | 360600 |
| BNC 082 | Burlington, NC | MRSA | 124 | 253400 | 346300 |
| BNC 083 | Burlington, NC | MRSA | 55 | 335000 | 26420 |
| BNC 084 | Burlington, NC | MRSA | 107 | 1147000 | 333700 |
| BNC 085 | Burlington, NC | MRSA | 60 | 1537000 | 197300 |
| BNC 086 | Burlington, NC | MRSA | 72 | 288600 | 320800 |
| BNC 087 | Burlington, NC | MRSA | 67 | 571900 | 453700 |
| BNC 088 | Burlington, NC | MRSA | 63 | 1197000 | 459600 |
| BNC 089 | Burlington, NC | MRSA | 67 | 610600 | 210900 |
| BNC 090 | Burlington, NC | MRSA | 87 | 615900 | 245200 |
| BNC 091 | Burlington, NC | MRSA | 77 | 1480000 | 452700 |
| BNC 092 | Burlington, NC | MRSA | 55 | 56460 | 4798 |
| BNC 093 | Burlington, NC | MRSA | 58 | 447600 | 68300 |
| BNC 094 | Burlington, NC | MRSA | 89 | 777300 | 127800 |
| BNC 095 | Burlington, NC | MRSA | 82 | 667100 | 88790 |
| BNC 096 | Burlington, NC | MRSA | 58 | 292400 | 277900 |
| BNC 097 | Burlington, NC | MRSA | 62 | 235000 | 3503 |
| BNC 098 | Burlington, NC | MRSA | 49 | 292400 | 108600 |
| BNC 099 | Burlington, NC | MRSA | 54 | 290500 | 81860 |
| BNC 100 | Burlington, NC | MRSA | 30 | 258700 | 200 |
| BNC 101 | Burlington, NC | MRSA | 34 | 9915 | 201 |
| BNC 102 | Burlington, NC | MRSA | 99 | 1417000 | 619600 |
| BNC 103 | Burlington, NC | MRSA | 30 | 960900 | 129000 |
| BNC 104 | Burlington, NC | MRSA | 32 | 24730 | 5909 |
| BNC 105 | Burlington, NC | MRSA | 72 | 65470 | 10800 |
| BNC 106 | Burlington, NC | MRSA | 47 | 461000 | 31660 |
| BNC 107 | Burlington, NC | MRSA | 28 | 1194000 | 110300 |
| BNC 108 | Burlington, NC | MRSA | 32 | 231000 | 78830 |
| BNC 109 | Burlington, NC | MRSA | 30 | 3896 | 1622 |
| BNC 110 | Burlington, NC | MRSA | 22 | 11350 | 3823 |
| BNC 111 | Burlington, NC | MRSA | 40 | 256800 | 71110 |
| BNC 112 | Burlington, NC | MRSA | 30 | 220500 | 1860 |
| BNC 113 | Burlington, NC | MRSA | 21 | 263000 | 63540 |
| BNC 114 | Burlington, NC | MRSA | 40 | 1239000 | 213000 |
| BNC 115 | Burlington, NC | MRSA | 88 | 403400 | 294800 |
| BNC 116 | Burlington, NC | MRSA | 119 | 1482000 | 539000 |
| BNC 117 | Burlington, NC | MRSA | 57 | 733700 | 882200 |
| BNC 118 | Burlington, NC | MRSA | 40 | 74430 | 30210 |
| BNC 119 | Burlington, NC | MRSA | 77 | 2284000 | 33230 |
| BNC 120 | Burlington, NC | MRSA | 89 | 1720000 | 1680000 |
| BNC 121 | Burlington, NC | MRSA | 71 | 1905000 | 1188000 |
| BNC 122 | Burlington, NC | MRSA | 56 | 1822000 | 585800 |
| BNC 123 | Burlington, NC | MRSA | 99 | 2689000 | 1325000 |
| BNC 124 | Burlington, NC | MRSA | 46 | 1278000 | 606200 |
| BNC 125 | Burlington, NC | MRSA | 66 | 802100 | 281100 |
| BNC 126 | Burlington, NC | MRSA | 49 | 277200 | 88590 |
| BNC 127 | Burlington, NC | MRSA | 41 | 335900 | 122000 |
| BNC 128 | Burlington, NC | MRSA | 60 | 1709000 | 348200 |
| BNC 129 | Burlington, NC | MRSA | 63 | 1054000 | 424400 |
| BNC 130 | Burlington, NC | MRSA | 95 | 1978000 | 591800 |
| BNC 131 | Burlington, NC | MRSA | 48 | 175600 | 50620 |
| BNC 132 | Burlington, NC | MRSA | 43 | 208000 | 35030 |

TABLE S4-continued

CFU and RLU for MRSA screen with clinical
*Staphylococcus aureus* (Table 4)

| Strain ID | Source | Type | CFU | Control RLU | Selective RLU |
|---|---|---|---|---|---|
| BNC 133 | Burlington, NC | MRSA | 36 | 197100 | 152800 |
| BNC 134 | Burlington, NC | MRSA | 62 | 395200 | 69230 |
| BNC 135 | Burlington, NC | MRSA | 60 | 516200 | 146000 |
| BNC 136 | Burlington, NC | MRSA | 23 | 29540 | 49420 |
| BNC 137 | Burlington, NC | MRSA | 28 | 114500 | 23060 |
| BNC 138 | Burlington, NC | MRSA | 46 | 418900 | 310100 |
| BNC 139 | Burlington, NC | MRSA | 42 | 304700 | 23260 |
| BNC 140 | Burlington, NC | MRSA | 32 | 510500 | 38020 |
| BNC 141 | Burlington, NC | MRSA | 48 | 124000 | 34990 |
| BNC 142 | Burlington, NC | MRSA | 152 | 1351000 | 195500 |
| BNC 143 | Burlington, NC | MRSA | 71 | 1461000 | 345000 |
| BNC 144 | Burlington, NC | MRSA | 85 | 1087000 | 121300 |
| BNC 145 | Burlington, NC | MRSA | 66 | 796300 | 156000 |
| BNC 146 | Burlington, NC | MRSA | 77 | 527500 | 142700 |
| BNC 147 | Burlington, NC | MRSA | 46 | 915500 | 141400 |
| BNC 148 | Burlington, NC | MRSA | 9 | 15650 | 2590 |
| BNC 149 | Burlington, NC | MRSA | 70 | 554300 | 73420 |
| BNC 150 | Burlington, NC | MRSA | 88 | 300300 | 56170 |
| BNC 151 | Burlington, NC | MRSA | 41 | 832900 | 217300 |
| BNC 152 | Burlington, NC | MRSA | 53 | 921300 | 8959 |
| BNC 153 | Burlington, NC | MRSA | 32 | 1144000 | 254100 |
| BNC 154 | Burlington, NC | MRSA | 44 | 700200 | 680 |
| BNC 155 | Burlington, NC | MRSA | 59 | 1015000 | 82570 |
| BNC 156 | Burlington, NC | MRSA | 79 | 560100 | 298100 |
| BNC 157 | Burlington, NC | MRSA | 42 | 523900 | 458300 |
| BNC 158 | Burlington, NC | MRSA | 40 | 974500 | 78210 |
| BNC 159 | Burlington, NC | MRSA | 27 | 116 | 116 |
| BNC 160 | Burlington, NC | MRSA | 44 | 940500 | 90170 |
| BNC 161 | Burlington, NC | MRSA | 37 | 150800 | 37390 |
| BNC 162 | Burlington, NC | MRSA | 49 | 576800 | 229000 |
| BNC 163 | Burlington, NC | MRSA | 54 | 509500 | 335 |
| BNC 164 | Burlington, NC | MRSA | 38 | 126300 | 9227 |
| BNC 165 | Burlington, NC | MRSA | 43 | 220300 | 73850 |
| BNC 166 | Burlington, NC | MRSA | 60 | 52120 | 11560 |
| BNC 167 | Burlington, NC | MRSA | 36 | 943400 | 136700 |
| BNC 168 | Burlington, NC | MRSA | 73 | 1015000 | 75970 |
| BNC 169 | Burlington, NC | MRSA | 88 | 408400 | 126400 |
| BNC 170 | Burlington, NC | MRSA | 102 | 857000 | 441400 |
| BNC 171 | Burlington, NC | MRSA | 21 | 59450 | 199200 |
| BNC 172 | Burlington, NC | MRSA | 35 | 1699000 | 202000 |
| BNC 173 | Burlington, NC | MRSA | 59 | 1823000 | 4858 |
| BNC 174 | Burlington, NC | MRSA | 42 | 1440000 | 101300 |
| BNC 175 | Burlington, NC | MRSA | 32 | 1348000 | 472100 |
| BNC 176 | Burlington, NC | MRSA | 49 | 1201000 | 819400 |
| BNC 177 | Burlington, NC | MRSA | 31 | 807900 | 161300 |
| BNC 178 | Burlington, NC | MRSA | 45 | 1473000 | 125500 |
| BNC 179 | Burlington, NC | MRSA | 22 | 231500 | 319800 |
| BNC 180 | Burlington, NC | MRSA | 50 | 1814000 | 739300 |
| BNC 181 | Burlington, NC | MRSA | 32 | 1731000 | 259400 |
| BNC 182 | Burlington, NC | MRSA | 50 | 763000 | 185900 |
| BNC 183 | Burlington, NC | MRSA | 37 | 1103000 | 96700 |
| BNC 184 | Burlington, NC | MRSA | 55 | 706900 | 321600 |
| BNC 185 | Burlington, NC | MRSA | 61 | 2111000 | 553400 |
| BNC 186 | Burlington, NC | MRSA | 80 | 783800 | 126200 |
| BNC 187 | Burlington, NC | MRSA | 117 | 3426000 | 211500 |
| BNC 188 | Burlington, NC | MRSA | 72 | 451100 | 362100 |
| BNC 189 | Burlington, NC | MRSA | 45 | 1372000 | 149200 |
| BNC 190 | Burlington, NC | MRSA | 86 | 3009000 | 321700 |
| BNC 191 | Burlington, NC | MRSA | 76 | 286600 | 10430 |
| BNC 192 | Burlington, NC | MRSA | 120 | 458400 | 90650 |
| BNC 193 | Burlington, NC | MRSA | 50 | 126300 | 7055 |
| BNC 194 | Burlington, NC | MRSA | 60 | 308000 | 15370 |
| BNC 195 | Burlington, NC | MRSA | 122 | 1826000 | 108100 |
| BNC 196 | Burlington, NC | MRSA | 68 | 2787000 | 888300 |
| BNC 197 | Burlington, NC | MRSA | 110 | 1654000 | 205500 |
| BNC 198 | Burlington, NC | MRSA | 74 | 347700 | 160700 |
| BNC 199 | Burlington, NC | MRSA | 57 | 1511000 | 180700 |
| BNC 200 | Burlington, NC | MRSA | 66 | 2263000 | 110800 |
| BNC 201 | Burlington, NC | MRSA | 92 | 1471000 | 74370 |
| BNC 202 | Burlington, NC | MRSA | 93 | 934700 | 220900 |
| BNC 203 | Burlington, NC | MRSA | 72 | 437700 | 551700 |
| BNC 204 | Burlington, NC | MRSA | 52 | 650900 | 141500 |
| BNC 205 | Burlington, NC | MRSA | 58 | 2123000 | 554600 |
| BNC 206 | Burlington, NC | MRSA | 72 | 1709000 | 61300 |
| BNC 207 | Burlington, NC | MRSA | 45 | 1147000 | 187900 |

TABLE S4-continued

CFU and RLU for MRSA screen with clinical
*Staphylococcus aureus* (Table 4)

TABLE S4-continued

CFU and RLU for MRSA screen with clinical
*Staphylococcus aureus* (Table 4)

| Strain ID | Source | Type | CFU | Control RLU | Selective RLU |
|-----------|--------|------|-----|-------------|---------------|
| PHX 003 | Phoenix, AZ | MRSA | 81 | 801800 | 359800 |
| PHX 004 | Phoenix, AZ | MRSA | 87 | 1038000 | 803100 |
| PHX 005 | Phoenix, AZ | MRSA | 112 | 171200 | 41110 |
| PHX 006 | Phoenix, AZ | MRSA | 87 | 1441000 | 172600 |
| PHX 007 | Phoenix, AZ | MRSA | 104 | 1227000 | 294200 |
| PHX 008 | Phoenix, AZ | MRSA | 108 | 2240000 | 656800 |
| PHX 009 | Phoenix, AZ | MRSA | 29 | 1268000 | 4035 |
| PHX 010 | Phoenix, AZ | MRSA | 34 | 535800 | 301600 |
| PHX 011 | Phoenix, AZ | MRSA | 44 | 794100 | 74050 |
| PHX 012 | Phoenix, AZ | MRSA | 27 | 21470 | 5567 |
| PHX 013 | Phoenix, AZ | MRSA | 35 | 1072000 | 64470 |
| PHX 014 | Phoenix, AZ | MRSA | 43 | 1414000 | 232200 |
| PHX 015 | Phoenix, AZ | MRSA | 46 | 1368000 | 412800 |
| PHX 016 | Phoenix, AZ | MRSA | 51 | 1473000 | 70650 |
| PHX 017 | Phoenix, AZ | MRSA | 35 | 1846000 | 371400 |
| PHX 019 | Phoenix, AZ | MRSA | 15 | 28730 | 1160 |
| PHX 020 | Phoenix, AZ | MRSA | 42 | 1185000 | 452100 |
| PHX 021 | Phoenix, AZ | MRSA | 75 | 310200 | 161100 |
| PHX 022 | Phoenix, AZ | MRSA | 52 | 2445000 | 769600 |
| PHX 023 | Phoenix, AZ | MRSA | 72 | 371400 | 198900 |
| PHX 024 | Phoenix, AZ | MRSA | 45 | 1120000 | 166400 |
| PHX 025 | Phoenix, AZ | MRSA | 16 | 120500 | 61620 |
| PHX 026 | Phoenix, AZ | MRSA | 7 | 1076000 | 120200 |
| PHX 027 | Phoenix, AZ | MRSA | 68 | 1282000 | 428100 |
| PHX 028 | Phoenix, AZ | MRSA | 66 | 1072000 | 425000 |
| PHX 029 | Phoenix, AZ | MRSA | 47 | 966500 | 238100 |
| PHX 030 | Phoenix, AZ | MRSA | 53 | 109300 | 8256 |
| PHX 031 | Phoenix, AZ | MRSA | 25 | 29020 | 1695 |
| PHX 032 | Phoenix, AZ | MRSA | 52 | 1163000 | 361900 |
| PHX 033 | Phoenix, AZ | MRSA | 20 | 1807000 | 364600 |
| PHX 034 | Phoenix, AZ | MRSA | 41 | 1075000 | 255100 |
| PHX 035 | Phoenix, AZ | MRSA | 29 | 827200 | 209100 |
| PHX 036 | Phoenix, AZ | MRSA | 29 | 95790 | 32800 |
| PHX 037 | Phoenix, AZ | MRSA | 45 | 184500 | 34990 |
| PHX 038 | Phoenix, AZ | MRSA | 58 | 212500 | 96450 |
| PHX 039 | Phoenix, AZ | MRSA | 64 | 360800 | 50240 |
| PHX 040 | Phoenix, AZ | MRSA | 28 | 1852000 | 819200 |
| PHX 041 | Phoenix, AZ | MRSA | 21 | 202400 | 6988 |
| PHX 042 | Phoenix, AZ | MRSA | 28 | 16570 | 860 |
| PHX 043 | Phoenix, AZ | MRSA | 41 | 1824000 | 716300 |
| PHX 044 | Phoenix, AZ | MRSA | 79 | 431300 | 79640 |
| PHX 045 | Phoenix, AZ | MRSA | 130 | 525900 | 148000 |
| PHX 046 | Phoenix, AZ | MRSA | 81 | 335800 | 61970 |
| PHX 047 | Phoenix, AZ | MRSA | 44 | 1420000 | 246700 |
| PHX 048 | Phoenix, AZ | MRSA | 39 | 143800 | 3399 |
| PHX 049 | Phoenix, AZ | MRSA | 40 | 1116000 | 147400 |
| PHX 050 | Phoenix, AZ | MRSA | 115 | 688400 | 130800 |
| PHX 051 | Phoenix, AZ | MRSA | 46 | 2213000 | 406000 |
| PHX 052 | Phoenix, AZ | MRSA | 67 | 8380 | 9214 |
| PHX 053 | Phoenix, AZ | MRSA | 87 | 824000 | 782 |
| PHX 054 | Phoenix, AZ | MRSA | 143 | 2480000 | 407800 |
| PHX 055 | Phoenix, AZ | MRSA | 82 | 2912000 | 1214000 |
| PHX 056 | Phoenix, AZ | MRSA | 53 | 306800 | 167500 |
| PHX 057 | Phoenix, AZ | MRSA | 44 | 1611000 | 430900 |
| PHX 058 | Phoenix, AZ | MRSA | 62 | 1386000 | 221300 |
| PHX 059 | Phoenix, AZ | MRSA | 101 | 2572000 | 949300 |
| PHX 060 | Phoenix, AZ | MRSA | 53 | 1594000 | 622800 |
| PHX 061 | Phoenix, AZ | MRSA | 65 | 108900 | 80590 |
| PHX 062 | Phoenix, AZ | MRSA | 16 | 1534000 | 24560 |
| PHX 063 | Phoenix, AZ | MRSA | 24 | 1041000 | 23500 |
| PHX 064 | Phoenix, AZ | MRSA | 19 | 1346000 | 67730 |
| PHX 065 | Phoenix, AZ | MRSA | 37 | 1076000 | 58500 |
| PHX 066 | Phoenix, AZ | MRSA | 41 | 1381000 | 171400 |
| PHX 067 | Phoenix, AZ | MRSA | 37 | 1501000 | 323600 |
| PHX 068 | Phoenix, AZ | MRSA | 35 | 342600 | 132900 |
| PHX 069 | Phoenix, AZ | MRSA | 106 | 1188000 | 155600 |
| PHX 070 | Phoenix, AZ | MRSA | 75 | 1182000 | 111500 |
| PHX 071 | Phoenix, AZ | MRSA | 84 | 140200 | 30350 |
| PHX 072 | Phoenix, AZ | MRSA | 9 | 86350 | 3319 |
| PHX 073 | Phoenix, AZ | MRSA | 31 | 224500 | 2761 |
| PHX 074 | Phoenix, AZ | MRSA | 51 | 1434000 | 510000 |
| PHX 075 | Phoenix, AZ | MRSA | 32 | 1474000 | 239800 |
| PHX 076 | Phoenix, AZ | MRSA | 58 | 544900 | 146400 |
| PHX 077 | Phoenix, AZ | MRSA | 49 | 295200 | 5176 |
| PHX 079 | Phoenix, AZ | MRSA | 58 | 582 | 251 |
| PHX 080 | Phoenix, AZ | MRSA | 44 | 276500 | 756 |
| PHX 081 | Phoenix, AZ | MRSA | 60 | 747000 | 92300 |
| PHX 082 | Phoenix, AZ | MRSA | 18 | 415900 | 50380 |
| PHX 083 | Phoenix, AZ | MRSA | 61 | 769500 | 477100 |
| PHX 084 | Phoenix, AZ | MRSA | 57 | 482800 | 173700 |
| PHX 085 | Phoenix, AZ | MRSA | 21 | 819100 | 988 |
| PHX 086 | Phoenix, AZ | MRSA | 20 | 16720 | 4286 |
| PHX 087 | Phoenix, AZ | MRSA | 40 | 491100 | 34790 |
| PHX 088 | Phoenix, AZ | MRSA | 28 | 986100 | 611400 |
| PHX 089 | Phoenix, AZ | MRSA | 17 | 923000 | 381100 |
| PHX 090 | Phoenix, AZ | MRSA | 32 | 1217000 | 75950 |
| PHX 091 | Phoenix, AZ | MRSA | 36 | 22040 | 1321 |
| PHX 092 | Phoenix, AZ | MRSA | 58 | 1093000 | 256800 |
| PHX 093 | Phoenix, AZ | MRSA | 61 | 1687000 | 565000 |
| PHX 094 | Phoenix, AZ | MRSA | 41 | 1611000 | 459200 |
| PHX 095 | Phoenix, AZ | MRSA | 1 | 14410 | 4688 |
| PHX 096 | Phoenix, AZ | MRSA | 32 | 481300 | 445900 |
| PHX 097 | Phoenix, AZ | MRSA | 55 | 1311000 | 70120 |
| PHX 098 | Phoenix, AZ | MRSA | 54 | 400400 | 241900 |
| PHX 099 | Phoenix, AZ | MRSA | 27 | 247600 | 26080 |
| PHX 100 | Phoenix, AZ | MRSA | 54 | 600100 | 12280 |
| RNJ 002 | Raritan, NJ | MRSA | 62 | 29810 | 16180 |
| RNJ 003 | Raritan, NJ | MRSA | 35 | 3892 | 3572 |
| RNJ 004 | Raritan, NJ | MRSA | 52 | 642500 | 66700 |
| RNJ 005 | Raritan, NJ | MRSA | 52 | 31490 | 615 |
| RNJ 006 | Raritan, NJ | MRSA | 59 | 44020 | 1850 |
| RNJ 007 | Raritan, NJ | MRSA | 38 | 354200 | 138600 |
| RNJ 008 | Raritan, NJ | MRSA | 24 | 254700 | 18220 |
| RNJ 009 | Raritan, NJ | MRSA | 29 | 23730 | 4994 |
| RNJ 010 | Raritan, NJ | MRSA | 40 | 84270 | 13800 |
| RNJ 011 | Raritan, NJ | MRSA | 49 | 930900 | 276600 |
| RNJ 013 | Raritan, NJ | MRSA | 43 | 437600 | 85070 |
| RNJ 014 | Raritan, NJ | MRSA | 63 | 214500 | 89000 |
| RNJ 015 | Raritan, NJ | MRSA | 58 | 160700 | 7251 |
| RNJ 016 | Raritan, NJ | MRSA | 30 | 213400 | 48850 |
| RNJ 017 | Raritan, NJ | MRSA | 61 | 1040000 | 121600 |
| RNJ 019 | Raritan, NJ | MRSA | 54 | 1665 | 555 |
| RNJ 020 | Raritan, NJ | MRSA | 25 | 353100 | 6338 |
| RNJ 021 | Raritan, NJ | MRSA | 26 | 163100 | 31140 |
| RNJ 022 | Raritan, NJ | MRSA | 44 | 267800 | 61040 |
| RNJ 023 | Raritan, NJ | MRSA | 30 | 1439000 | 117700 |
| RNJ 024 | Raritan, NJ | MRSA | 17 | 434000 | 2368 |
| RNJ 025 | Raritan, NJ | MRSA | 76 | 31360 | 1928 |
| RNJ 026 | Raritan, NJ | MRSA | 34 | 779200 | 21940 |
| RNJ 027 | Raritan, NJ | MRSA | 23 | 1209000 | 115500 |
| RNJ 028 | Raritan, NJ | MRSA | 51 | 1016000 | 255000 |
| RNJ 029 | Raritan, NJ | MRSA | 74 | 221900 | 54640 |
| RNJ 030 | Raritan, NJ | MRSA | 28 | 390600 | 126900 |
| RNJ 031 | Raritan, NJ | MRSA | 59 | 230900 | 105700 |
| RNJ 033 | Raritan, NJ | MRSA | 44 | 768600 | 395500 |
| RNJ 034 | Raritan, NJ | MRSA | 83 | 560700 | 61870 |
| RNJ 035 | Raritan, NJ | MRSA | 64 | 1620000 | 320000 |
| RNJ 036 | Raritan, NJ | MRSA | 59 | 752200 | 157100 |
| RNJ 037 | Raritan, NJ | MRSA | 5 | 583000 | 111500 |
| RNJ 038 | Raritan, NJ | MRSA | 81 | 1206000 | 182100 |
| RNJ 039 | Raritan, NJ | MRSA | 33 | 1107000 | 4091 |
| RNJ 040 | Raritan, NJ | MRSA | 59 | 6722 | 2635 |
| RNJ 041 | Raritan, NJ | MRSA | 39 | 651100 | 466 |
| RNJ 042 | Raritan, NJ | MRSA | 34 | 375500 | 64700 |
| RNJ 043 | Raritan, NJ | MRSA | 31 | 1331000 | 160000 |
| RNJ 044 | Raritan, NJ | MRSA | 45 | 1941000 | 298400 |
| RNJ 045 | Raritan, NJ | MRSA | 12 | 1499000 | 293600 |
| RNJ 046 | Raritan, NJ | MRSA | 53 | 695600 | 266500 |
| RNJ 047 | Raritan, NJ | MRSA | 40 | 938000 | 168200 |
| RNJ 048 | Raritan, NJ | MRSA | 67 | 1339000 | 265200 |
| RNJ 049 | Raritan, NJ | MRSA | 33 | 376500 | 132000 |
| RNJ 050 | Raritan, NJ | MRSA | 17 | 325100 | 2277 |
| RNJ 051 | Raritan, NJ | MRSA | 48 | 791500 | 667500 |
| RNJ 052 | Raritan, NJ | MRSA | 58 | 659900 | 375000 |
| RNJ 053 | Raritan, NJ | MRSA | 55 | 2820000 | 759100 |
| RNJ 054 | Raritan, NJ | MRSA | 53 | 415200 | 70710 |
| RNJ 055 | Raritan, NJ | MRSA | 26 | 822600 | 167700 |
| RNJ 056 | Raritan, NJ | MRSA | 65 | 1421000 | 60460 |
| RNJ 057 | Raritan, NJ | MRSA | 34 | 1070000 | 251600 |
| RNJ 058 | Raritan, NJ | MRSA | 34 | 1700000 | 326400 |

TABLE S4-continued

CFU and RLU for MRSA screen with clinical
*Staphylococcus aureus* (Table 4)

| Strain ID | Source | Type | CFU | Control RLU | Selective RLU |
|---|---|---|---|---|---|
| RNJ 063 | Raritan, NJ | MRSA | 45 | 742200 | 173000 |
| RNJ 064 | Raritan, NJ | MRSA | 26 | 431600 | 91070 |
| RNJ 067 | Raritan, NJ | MRSA | 40 | 1264000 | 326800 |
| RNJ 068 | Raritan, NJ | MRSA | 31 | 1492000 | 976600 |
| RNJ 069 | Raritan, NJ | MRSA | 24 | 500000 | 356000 |
| RNJ 070 | Raritan, NJ | MRSA | 43 | 1720000 | 197700 |
| RNJ 072 | Raritan, NJ | MRSA | 29 | 389700 | 172700 |
| RNJ 073 | Raritan, NJ | MRSA | 25 | 391600 | 103700 |
| RNJ 074 | Raritan, NJ | MRSA | 56 | 1484000 | 522600 |
| RNJ 075 | Raritan, NJ | MRSA | 48 | 1287000 | 46680 |
| RNJ 076 | Raritan, NJ | MRSA | 55 | 3062000 | 41000 |
| RNJ 077 | Raritan, NJ | MRSA | 51 | 457500 | 501100 |
| RNJ 078 | Raritan, NJ | MRSA | 56 | 1717000 | 702100 |
| RNJ 079 | Raritan, NJ | MRSA | 63 | 396300 | 116600 |
| RNJ 080 | Raritan, NJ | MRSA | 45 | 889400 | 291400 |
| RNJ 081 | Raritan, NJ | MRSA | 45 | 214200 | 85150 |
| RNJ 082 | Raritan, NJ | MRSA | 84 | 418900 | 100300 |
| RNJ 083 | Raritan, NJ | MRSA | 61 | 9127 | 1862 |
| RNJ 084 | Raritan, NJ | MRSA | 27 | 42700 | 7484 |
| RNJ 085 | Raritan, NJ | MRSA | 32 | 66280 | 7761 |
| RNJ 086 | Raritan, NJ | MRSA | 37 | 849200 | 98460 |
| RNJ 087 | Raritan, NJ | MRSA | 75 | 277800 | 104300 |
| RNJ 088 | Raritan, NJ | MRSA | 24 | 390600 | 40130 |
| RNJ 089 | Raritan, NJ | MRSA | 26 | 757500 | 81980 |
| RNJ 090 | Raritan, NJ | MRSA | 45 | 1142000 | 99340 |
| RNJ 091 | Raritan, NJ | MRSA | 33 | 457500 | 38900 |
| RNJ 092 | Raritan, NJ | MRSA | 51 | 720300 | 81470 |
| RNJ 093 | Raritan, NJ | MRSA | 15 | 92420 | 23290 |
| RNJ 094 | Raritan, NJ | MRSA | 20 | 615000 | 20570 |
| RNJ 095 | Raritan, NJ | MRSA | 116 | 1033000 | 53080 |
| RNJ 096 | Raritan, NJ | MRSA | 53 | 475800 | 22780 |
| RNJ 097 | Raritan, NJ | MRSA | 53 | 1277000 | 105100 |
| RNJ 098 | Raritan, NJ | MRSA | 54 | 430900 | 32150 |
| RNJ 099 | Raritan, NJ | MRSA | 64 | 534900 | 195100 |
| RNJ 100 | Raritan, NJ | MRSA | 48 | 1680000 | 398200 |
| MSSA 001 | Burlington, NC | MSSA | 1115 | 60090000 | 142 |
| MSSA 001 | Burlington, NC | MSSA | 11150 | 191600000 | 151 |
| MSSA 002 | Burlington, NC | MSSA | 1030 | 22240000 | 142 |
| MSSA 002 | Burlington, NC | MSSA | 10300 | 103900000 | 302 |
| MSSA 003 | Burlington, NC | MSSA | 555 | 1107000 | 152 |
| MSSA 003 | Burlington, NC | MSSA | 5550 | 588700 | 256 |
| MSSA 004 | Burlington, NC | MSSA | 520 | 505800 | 172 |
| MSSA 004 | Burlington, NC | MSSA | 5200 | 658000 | 167 |
| MSSA 005 | Burlington, NC | MSSA | 760 | 26650000 | 156 |
| MSSA 005 | Burlington, NC | MSSA | 7600 | 218500000 | 826 |
| MSSA 006 | Burlington, NC | MSSA | 850 | 17170000 | 271 |
| MSSA 006 | Burlington, NC | MSSA | 8500 | 102100000 | 1296 |
| MSSA 007 | Burlington, NC | MSSA | 890 | 30170000 | 130 |
| MSSA 007 | Burlington, NC | MSSA | 8900 | 173300000 | 192 |
| MSSA 008 | Burlington, NC | MSSA | 495 | 32320000 | 130 |
| MSSA 008 | Burlington, NC | MSSA | 4950 | 178400000 | 355 |
| MSSA 009 | Burlington, NC | MSSA | 975 | 10060000 | 131 |
| MSSA 009 | Burlington, NC | MSSA | 9750 | 105400000 | 133 |
| MSSA 010 | Burlington, NC | MSSA | 530 | 584200 | 143 |
| MSSA 010 | Burlington, NC | MSSA | 5300 | 16930000 | 145 |
| MSSA 012 | Burlington, NC | MSSA | 1505 | 844200 | 145 |
| MSSA 012 | Burlington, NC | MSSA | 15050 | 228400 | 152 |
| MSSA 013 | Burlington, NC | MSSA | 685 | 8570000 | 151 |
| MSSA 013 | Burlington, NC | MSSA | 6850 | 69550000 | 130 |
| MSSA 014 | Burlington, NC | MSSA | 725 | 5493000 | 211 |
| MSSA 014 | Burlington, NC | MSSA | 7250 | 32060000 | 783 |
| MSSA 015 | Burlington, NC | MSSA | 835 | 5210000 | 160 |
| MSSA 015 | Burlington, NC | MSSA | 8350 | 61260000 | 153 |
| MSSA 016 | Burlington, NC | MSSA | 640 | 4549000 | 153 |
| MSSA 016 | Burlington, NC | MSSA | 6400 | 69860000 | 187 |
| MSSA 017 | Burlington, NC | MSSA | 615 | 11440000 | 160 |
| MSSA 017 | Burlington, NC | MSSA | 6150 | 80940000 | 140 |
| MSSA 018 | Burlington, NC | MSSA | 800 | 8989000 | 133 |
| MSSA 018 | Burlington, NC | MSSA | 8000 | 86910000 | 210 |
| MSSA 019 | Burlington, NC | MSSA | 750 | 5678000 | 155 |
| MSSA 019 | Burlington, NC | MSSA | 7500 | 47380000 | 221 |
| MSSA 020 | Burlington, NC | MSSA | 770 | 5347000 | 171 |
| MSSA 020 | Burlington, NC | MSSA | 7700 | 60860000 | 568 |
| MSSA 021 | Burlington, NC | MSSA | 820 | 5190000 | 142 |
| MSSA 021 | Burlington, NC | MSSA | 8200 | 51500000 | 180 |
| MSSA 022 | Burlington, NC | MSSA | 515 | 4629000 | 147 |
| MSSA 022 | Burlington, NC | MSSA | 5150 | 40440000 | 115 |
| MSSA 023 | Burlington, NC | MSSA | 1190 | 3793000 | 152 |
| MSSA 023 | Burlington, NC | MSSA | 11900 | 37420000 | 201 |
| MSSA 024 | Burlington, NC | MSSA | 840 | 10200000 | 186 |
| MSSA 024 | Burlington, NC | MSSA | 8400 | 71780000 | 228 |
| MSSA 025 | Burlington, NC | MSSA | 5840 | 50060000 | 143 |
| MSSA 025 | Burlington, NC | MSSA | 58400 | 9237000 | 257 |
| MSSA 026 | Burlington, NC | MSSA | 967 | 15230000 | 121 |
| MSSA 026 | Burlington, NC | MSSA | 9669 | 143300000 | 2617 |
| MSSA 027 | Burlington, NC | MSSA | 574 | 5188000 | 111 |
| MSSA 027 | Burlington, NC | MSSA | 5739 | 24030000 | 135 |
| MSSA 028 | Burlington, NC | MSSA | 392 | 30070000 | 166 |
| MSSA 028 | Burlington, NC | MSSA | 3918 | 116000000 | 3060 |
| MSSA 029 | Burlington, NC | MSSA | 815 | 26130000 | 205 |
| MSSA 029 | Burlington, NC | MSSA | 8146 | 186600000 | 2990 |
| MSSA 030 | Burlington, NC | MSSA | 602 | 7841000 | 150 |
| MSSA 030 | Burlington, NC | MSSA | 6021 | 20930000 | 115 |
| MSSA 031 | Burlington, NC | MSSA | 585 | 65420000 | 126 |
| MSSA 031 | Burlington, NC | MSSA | 5850 | 173000000 | 221 |
| MSSA 032 | Burlington, NC | MSSA | 691 | 482400 | 118 |
| MSSA 032 | Burlington, NC | MSSA | 6905 | 692000 | 112 |
| MSSA 033 | Burlington, NC | MSSA | 75 | 32220000 | 51460 |
| MSSA 033 | Burlington, NC | MSSA | 750 | 2769000 | 991900 |
| MSSA 034 | Burlington, NC | MSSA | 665 | 81260 | 1785 |
| MSSA 034 | Burlington, NC | MSSA | 6650 | 662100 | 22640 |
| MSSA 035 | Burlington, NC | MSSA | 890 | 9391000 | 110 |
| MSSA 035 | Burlington, NC | MSSA | 8900 | 21660000 | 123 |
| MSSA 036 | Burlington, NC | MSSA | 650 | 14430000 | 110 |
| MSSA 036 | Burlington, NC | MSSA | 6500 | 116500000 | 130 |
| MSSA 037 | Burlington, NC | MSSA | 1310 | 99810000 | 155 |
| MSSA 037 | Burlington, NC | MSSA | 13100 | 139200000 | 127 |
| MSSA 038 | Burlington, NC | MSSA | 2650 | 19110000 | 135 |
| MSSA 038 | Burlington, NC | MSSA | 26500 | 4454000 | 138 |
| MSSA 040 | Burlington, NC | MSSA | 630 | 19320000 | 142 |
| MSSA 040 | Burlington, NC | MSSA | 6300 | 130600000 | 262 |
| MSSA 041 | Burlington, NC | MSSA | 575 | 6440000 | 136 |
| MSSA 041 | Burlington, NC | MSSA | 5750 | 11370000 | 127 |
| MSSA 042 | Burlington, NC | MSSA | 1065 | 17930000 | 93 |
| MSSA 042 | Burlington, NC | MSSA | 10650 | 148500000 | 123 |
| MSSA 043 | Burlington, NC | MSSA | 1135 | 11780 | 105 |
| MSSA 043 | Burlington, NC | MSSA | 11350 | 9546 | 138 |
| MSSA 044 | Burlington, NC | MSSA | 675 | 35030000 | 126 |
| MSSA 044 | Burlington, NC | MSSA | 6750 | 22690000 | 125 |
| MSSA 045 | Burlington, NC | MSSA | 380 | 117500000 | 138 |
| MSSA 045 | Burlington, NC | MSSA | 3800 | 127500000 | 198 |
| MSSA 046 | Burlington, NC | MSSA | 1820 | 21270000 | 6603 |
| MSSA 046 | Burlington, NC | MSSA | 18200 | 83650000 | 51970 |
| MSSA 047 | Burlington, NC | MSSA | 525 | 12970000 | 101 |
| MSSA 047 | Burlington, NC | MSSA | 5250 | 112400000 | 130 |
| MSSA 048 | Burlington, NC | MSSA | 605 | 80400 | 127 |
| MSSA 048 | Burlington, NC | MSSA | 6050 | 112400 | 142 |
| MSSA 049 | Burlington, NC | MSSA | 1155 | 9999000 | 111 |
| MSSA 049 | Burlington, NC | MSSA | 11550 | 94090000 | 127 |
| MSSA 051 | Burlington, NC | MSSA | 1070 | 49090000 | 102 |
| MSSA 051 | Burlington, NC | MSSA | 10698 | 166400000 | 230 |
| MSSA 052 | Burlington, NC | MSSA | 1027 | 58950 | 118 |
| MSSA 052 | Burlington, NC | MSSA | 10273 | 63240 | 6854 |
| MSSA 053 | Burlington, NC | MSSA | 2470 | 13200000 | 136 |
| MSSA 053 | Burlington, NC | MSSA | 24700 | 1841000 | 116 |
| MSSA 054 | Burlington, NC | MSSA | 1163 | 21280000 | 141 |
| MSSA 054 | Burlington, NC | MSSA | 11626 | 95230000 | 242 |
| MSSA 055 | Burlington, NC | MSSA | 524 | 32020 | 122 |
| MSSA 055 | Burlington, NC | MSSA | 5244 | 397100 | 143 |
| MSSA 056 | Burlington, NC | MSSA | 1645 | 167500 | 115 |
| MSSA 056 | Burlington, NC | MSSA | 16445 | 139800 | 216 |
| MSSA 057 | Burlington, NC | MSSA | 4010 | 354000 | 140 |
| MSSA 057 | Burlington, NC | MSSA | 40100 | 89330 | 127 |
| MSSA 058 | Burlington, NC | MSSA | 834 | 23450000 | 191 |
| MSSA 058 | Burlington, NC | MSSA | 8337 | 164100000 | 403 |
| MSSA 059 | Burlington, NC | MSSA | 620 | 4902000 | 146 |
| MSSA 059 | Burlington, NC | MSSA | 6200 | 3845000 | 195 |
| MSSA 060 | Burlington, NC | MSSA | 600 | 28390000 | 137 |
| MSSA 060 | Burlington, NC | MSSA | 6000 | 236600000 | 131 |
| MSSA 062 | Burlington, NC | MSSA | 590 | 29090000 | 173 |

TABLE S4-continued

CFU and RLU for MRSA screen with clinical
*Staphylococcus aureus* (Table 4)

| Strain ID | Source | Type | CFU | Control RLU | Selective RLU |
|---|---|---|---|---|---|
| MSSA 062 | Burlington, NC | MSSA | 5900 | 186300000 | 145 |
| MSSA 063 | Burlington, NC | MSSA | 835 | 32080000 | 151 |
| MSSA 063 | Burlington, NC | MSSA | 8350 | 16880000 | 227 |
| MSSA 064 | Burlington, NC | MSSA | 730 | 11270000 | 117 |
| MSSA 064 | Burlington, NC | MSSA | 7300 | 96400000 | 152 |
| MSSA 065 | Burlington, NC | MSSA | 850 | 4029000 | 125 |
| MSSA 065 | Burlington, NC | MSSA | 8500 | 32560000 | 223 |
| MSSA 066 | Burlington, NC | MSSA | 915 | 26320000 | 123 |
| MSSA 066 | Burlington, NC | MSSA | 9150 | 182100000 | 208 |
| MSSA 067 | Burlington, NC | MSSA | 895 | 509900 | 125 |
| MSSA 067 | Burlington, NC | MSSA | 8950 | 224900 | 122 |
| MSSA 068 | Burlington, NC | MSSA | 1215 | 22720000 | 647 |
| MSSA 068 | Burlington, NC | MSSA | 12150 | 123100000 | 6137 |
| MSSA 070 | Burlington, NC | MSSA | 850 | 2636000 | 140 |
| MSSA 070 | Burlington, NC | MSSA | 8500 | 2484000 | 243 |
| MSSA 071 | Burlington, NC | MSSA | 940 | 32020000 | 101 |
| MSSA 071 | Burlington, NC | MSSA | 9400 | 200800000 | 153 |
| MSSA 072 | Burlington, NC | MSSA | 555 | 12640000 | 132 |
| MSSA 072 | Burlington, NC | MSSA | 5550 | 35260000 | 191 |
| MSSA 073 | Burlington, NC | MSSA | 1240 | 146000000 | 257 |
| MSSA 073 | Burlington, NC | MSSA | 12400 | 153900000 | 986 |
| MSSA 074 | Burlington, NC | MSSA | 795 | 38360000 | 127 |
| MSSA 074 | Burlington, NC | MSSA | 7950 | 204600000 | 241 |
| MSSA 075 | Burlington, NC | MSSA | 505 | 2452000 | 135 |
| MSSA 075 | Burlington, NC | MSSA | 5050 | 4719000 | 155 |
| MSSA 076 | Burlington, NC | MSSA | 560 | 26460000 | 155 |
| MSSA 076 | Burlington, NC | MSSA | 5600 | 19290000 | 143 |
| MSSA 077 | Burlington, NC | MSSA | 612 | 13580 | 136 |
| MSSA 077 | Burlington, NC | MSSA | 6117 | 114600 | 146 |
| MSSA 078 | Burlington, NC | MSSA | 600 | 12790000 | 237 |
| MSSA 078 | Burlington, NC | MSSA | 5996 | 111100000 | 176 |
| MSSA 079 | Burlington, NC | MSSA | 845 | 3778000 | 1992 |
| MSSA 079 | Burlington, NC | MSSA | 8450 | 468000 | 69570 |
| MSSA 081 | Burlington, NC | MSSA | 508 | 3471000 | 143 |
| MSSA 081 | Burlington, NC | MSSA | 5082 | 10920000 | 178 |
| MSSA 082 | Burlington, NC | MSSA | 1190 | 752100 | 146 |
| MSSA 082 | Burlington, NC | MSSA | 11903 | 1879000 | 2578 |
| MSSA 083 | Burlington, NC | MSSA | 1241 | 8341000 | 157 |
| MSSA 083 | Burlington, NC | MSSA | 12413 | 7199000 | 251 |
| MSSA 084 | Burlington, NC | MSSA | 653 | 19390000 | 127 |
| MSSA 084 | Burlington, NC | MSSA | 6533 | 220200000 | 19330 |
| MSSA 085 | Burlington, NC | MSSA | 1795 | 99440000 | 150 |
| MSSA 085 | Burlington, NC | MSSA | 17950 | 146200000 | 163 |
| MSSA 086 | Burlington, NC | MSSA | 520 | 49250000 | 2293 |
| MSSA 086 | Burlington, NC | MSSA | 5200 | 105600000 | 493 |
| MSSA 087 | Burlington, NC | MSSA | 1775 | 3066000 | 146 |
| MSSA 087 | Burlington, NC | MSSA | 17750 | 685800 | 121 |
| MSSA 088 | Burlington, NC | MSSA | 560 | 30040000 | 146 |
| MSSA 088 | Burlington, NC | MSSA | 5600 | 206200000 | 150 |
| MSSA 089 | Burlington, NC | MSSA | 530 | 36470000 | 127 |
| MSSA 089 | Burlington, NC | MSSA | 5300 | 42370000 | 146 |
| MSSA 090 | Burlington, NC | MSSA | 2665 | 410 | 136 |
| MSSA 090 | Burlington, NC | MSSA | 26650 | 362 | 132 |
| MSSA 092 | Burlington, NC | MSSA | 1720 | 12890000 | 242 |
| MSSA 092 | Burlington, NC | MSSA | 17200 | 9981000 | 151 |
| MSSA 093 | Burlington, NC | MSSA | 815 | 13200000 | 146 |
| MSSA 093 | Burlington, NC | MSSA | 8150 | 139500000 | 147 |
| MSSA 094 | Burlington, NC | MSSA | 540 | 30770000 | 308 |
| MSSA 094 | Burlington, NC | MSSA | 5400 | 217700000 | 2002 |
| MSSA 095 | Burlington, NC | MSSA | 550 | 3105000 | 148 |
| MSSA 095 | Burlington, NC | MSSA | 5500 | 6685000 | 163 |
| MSSA 096 | Burlington, NC | MSSA | 520 | 4198000 | 137 |
| MSSA 096 | Burlington, NC | MSSA | 5200 | 1380000 | 223 |
| MSSA 097 | Burlington, NC | MSSA | 1075 | 38180000 | 141 |
| MSSA 097 | Burlington, NC | MSSA | 10750 | 173600000 | 145 |
| MSSA 098 | Burlington, NC | MSSA | 620 | 92970000 | 160 |
| MSSA 098 | Burlington, NC | MSSA | 6200 | 112700000 | 192 |
| MSSA 099 | Burlington, NC | MSSA | 500 | 25140000 | 138 |
| MSSA 099 | Burlington, NC | MSSA | 5000 | 14820000 | 133 |
| MSSA 100 | Burlington, NC | MSSA | 2465 | 665900 | 161 |
| MSSA 100 | Burlington, NC | MSSA | 24650 | 261600 | 131 |
| MSSA 101 | Burlington, NC | MSSA | 1775 | 17240000 | 640 |
| MSSA 101 | Burlington, NC | MSSA | 17750 | 100700000 | 6379 |
| MSSA 102 | Burlington, NC | MSSA | 1305 | 57270000 | 116 |
| MSSA 102 | Burlington, NC | MSSA | 13050 | 123300000 | 196 |

TABLE S4-continued

CFU and RLU for MRSA screen with clinical
*Staphylococcus aureus* (Table 4)

| Strain ID | Source | Type | CFU | Control RLU | Selective RLU |
|---|---|---|---|---|---|
| MSSA 103 | Burlington, NC | MSSA | 1310 | 659300 | 111 |
| MSSA 103 | Burlington, NC | MSSA | 13100 | 1076000 | 202 |
| MSSA 104 | Burlington, NC | MSSA | 865 | 122100000 | 163 |
| MSSA 104 | Burlington, NC | MSSA | 8650 | 196100000 | 230 |
| MSSA 105 | Burlington, NC | MSSA | 605 | 233100 | 260 |
| MSSA 105 | Burlington, NC | MSSA | 6050 | 3094000 | 401 |
| MSSA 106 | Burlington, NC | MSSA | 2170 | 294600 | 138 |
| MSSA 106 | Burlington, NC | MSSA | 21700 | 1219000 | 233 |
| MSSA 107 | Burlington, NC | MSSA | 2170 | 58870000 | 131 |
| MSSA 107 | Burlington, NC | MSSA | 21700 | 178100000 | 187 |
| MSSA 108 | Burlington, NC | MSSA | 1470 | 34780000 | 121 |
| MSSA 108 | Burlington, NC | MSSA | 14700 | 16800000 | 150 |
| MSSA 109 | Burlington, NC | MSSA | 1075 | 211400 | 127 |
| MSSA 109 | Burlington, NC | MSSA | 10750 | 193200 | 141 |
| MSSA 110 | Burlington, NC | MSSA | 1940 | 105800000 | 141 |
| MSSA 110 | Burlington, NC | MSSA | 19400 | 157500000 | 148 |
| MSSA 111 | Burlington, NC | MSSA | 1295 | 64950000 | 142 |
| MSSA 111 | Burlington, NC | MSSA | 12950 | 163300000 | 150 |
| MSSA 112 | Burlington, NC | MSSA | 1715 | 69600000 | 142 |
| MSSA 112 | Burlington, NC | MSSA | 17150 | 96770000 | 447 |
| MSSA 114 | Burlington, NC | MSSA | 2650 | 29930000 | 167 |
| MSSA 114 | Burlington, NC | MSSA | 26500 | 80920000 | 276 |
| MSSA 115 | Burlington, NC | MSSA | 1240 | 7031000 | 3608 |
| MSSA 115 | Burlington, NC | MSSA | 12400 | 1038000 | 22410 |
| MSSA 116 | Burlington, NC | MSSA | 660 | 14330000 | 132 |
| MSSA 116 | Burlington, NC | MSSA | 6600 | 7542000 | 838 |
| MSSA 117 | Burlington, NC | MSSA | 1575 | 32730000 | 117 |
| MSSA 117 | Burlington, NC | MSSA | 15750 | 17000000 | 281 |
| MSSA 118 | Burlington, NC | MSSA | 370 | 31230000 | 127 |
| MSSA 118 | Burlington, NC | MSSA | 3700 | 96050000 | 140 |
| MSSA 119 | Burlington, NC | MSSA | 1260 | 2231000 | 180 |
| MSSA 119 | Burlington, NC | MSSA | 12600 | 31030000 | 536 |
| MSSA 120 | Burlington, NC | MSSA | 1690 | 1872000 | 132 |
| MSSA 120 | Burlington, NC | MSSA | 16900 | 78730000 | 120 |
| MSSA 121 | Burlington, NC | MSSA | 1010 | 105100000 | 187 |
| MSSA 121 | Burlington, NC | MSSA | 10100 | 164900000 | 940 |
| MSSA 122 | Burlington, NC | MSSA | 755 | 57600000 | 181 |
| MSSA 122 | Burlington, NC | MSSA | 7550 | 29350000 | 553 |
| MSSA 123 | Burlington, NC | MSSA | 910 | 68570000 | 138 |
| MSSA 123 | Burlington, NC | MSSA | 9100 | 253500000 | 147 |
| MSSA 124 | Burlington, NC | MSSA | 1695 | 79390000 | 153 |
| MSSA 124 | Burlington, NC | MSSA | 16950 | 137800000 | 135 |
| MSSA 127 | Burlington, NC | MSSA | 2705 | 26150000 | 572 |
| MSSA 127 | Burlington, NC | MSSA | 27050 | 9820000 | 547 |
| MSSA 128 | Burlington, NC | MSSA | 950 | 39710000 | 245 |
| MSSA 128 | Burlington, NC | MSSA | 9500 | 175000000 | 1935 |
| MSSA 129 | Burlington, NC | MSSA | 1315 | 16500000 | 153 |
| MSSA 129 | Burlington, NC | MSSA | 13150 | 23170000 | 157 |
| MSSA 130 | Burlington, NC | MSSA | 1465 | 43860000 | 105 |
| MSSA 130 | Burlington, NC | MSSA | 14650 | 148700000 | 153 |
| MSSA 131 | Burlington, NC | MSSA | 1250 | 39310000 | 140 |
| MSSA 131 | Burlington, NC | MSSA | 12500 | 24780000 | 153 |
| MSSA 132 | Burlington, NC | MSSA | 1545 | 54710000 | 167 |
| MSSA 132 | Burlington, NC | MSSA | 15450 | 27560000 | 338 |
| MSSA 133 | Burlington, NC | MSSA | 1245 | 51020000 | 172 |
| MSSA 133 | Burlington, NC | MSSA | 12450 | 188000000 | 206 |

Example 4. Specificity and Screen Performance with Human Nasal Swabs

Anterior nasal specimens were self-collected from 40 adult human volunteers using a rayon swab. Previous studies have confirmed the efficacy of self-collection for the detection of MRSA colonization. Prior to processing, specimens were stored over-night at 4° C. to mimic possible sample shipping conditions. A reference method using both direct plating and enriched culture was employed to identify true MRSA colonization. All 40 human nasal specimens were negative by both reference methods and were determined to lack MRSA colonization (Table 5). The lack of detection among 40 individuals is not surprising, as the rate of MRSA colonization among healthy adults has been estimated at less than 2%.

To perform the screen with these specimens, the swab was eluted into bacterial culture media and added to wells with (selective) or without (control) cefoxitin. A positive result in the selective condition is considered to be a positive MRSA result. The control condition is not required or utilized for MRSA determination, but was included to demonstrate the effectiveness of selection. A positive result was anticipated in most control wells due to the high nasal colonization rates of *Staphylococcal* species and the cross-reactivity previously described with the phage cocktail. As expected, 36 of 40 (90%) samples were positive in the control well. RLU values for endogenous samples are provided (Table S5).

36 of 40 specimens (90.0%) were negative for MRSA detection and agreed with the reference method. False positives were identified in four samples, with a median RLU signal of less than five times the signal cutoff. All nasal samples were negative when tested directly with luciferase substrate, indicating that non-specific autoluminescence was not a significant source of false positives (Table S5). The exact mechanism behind the false positive signal in these samples remains unknown, but could potentially be linked to methicillin-resistant coagulase-negative *Staphylococci*.

Additionally, some MSSA strains were previously observed to result in false positive results at high bacterial burdens (Table 4). Overall, the majority (90%) of MRSA-negative samples could be successfully screened out by this method.

TABLE 5

| Screen performance with non-colonized nasal swabs | | | | | |
| --- | --- | --- | --- | --- | --- |
| | Endogenous Nasal Samples[2] (Elutant only) | | | Detection in Nasal Matrix[3] (Elutant + MRSA) | |
| | Control | Selective | Reference[4] | Control | Selective |
| Number of positives[1] (%): | 36/40 (90.0) | 4/40 (10.0) | 0/40 (0.0) | 40/40 (100) | 40/40 (100) |

[1]Positive wells were defined based on a signal cutoff of 600 RLU.

[2]Nasal swabs were eluted in bacterial culture media and assayed directly.

[3]Nasal elutants were spiked with one of five MRSA strains at approximately 100 CFU per well before testing.

[4]A combination of direct plating and enriched cultures was employed as a reference method using MRSA Select II agar.

TABLE S5

| CFU and RLU for nasal swabs: endogenous, MRSA spike, and autoluminescence (Table 5) | | | | | | | |
| --- | --- | --- | --- | --- | --- | --- | --- |
| | RLU for Endogenous[1] (Elutant only) | | RLU for MRSA Spike[2] (Elutant + MRSA) | | | | RLU for Autoluminescence[3] (No luciferase) |
| Swab # | Control | Selective | Strain | CFU[4] | Control | Selective | — |
| 1 | 745100 | 451 | BAA-1707 | 65 | 4932000 | 199400 | 331 |
| 2 | 161 | 163 | BAA-1707 | 65 | 3183000 | 1955000 | 22 |
| 3 | 227 | 193 | BAA-1707 | 65 | 2070000 | 339500 | 72 |
| 4 | 4778 | 197 | BAA-1707 | 65 | 3371000 | 1353000 | 41 |
| 5 | 19310 | 215 | BAA-1707 | 65 | 4343000 | 1564000 | 30 |
| 6 | 8334 | 240 | BAA-1707 | 65 | 4523000 | 991800 | 33 |
| 7 | 7619 | 195 | BAA-1707 | 65 | 3153000 | 1167000 | 47 |
| 8 | 34800 | 171 | BAA-1707 | 65 | 4569000 | 1178000 | 30 |
| 9 | 54630 | 225 | BAA-1717 | 105 | 2226000 | 167600 | 115 |
| 10 | 28380 | 198 | BAA-1717 | 105 | 4176000 | 756500 | 33 |
| 11 | 56130 | 1081 | BAA-1717 | 105 | 2877000 | 267300 | 58 |
| 12 | 6182 | 200 | BAA-1717 | 105 | 4740000 | 467100 | 62 |
| 13 | 1536000 | 6505 | BAA-1717 | 105 | 1714000 | 196300 | 153 |
| 14 | 27190 | 150 | BAA-1717 | 105 | 2649000 | 288100 | 23 |
| 15 | 8236 | 157 | BAA-1717 | 105 | 3584000 | 423200 | 23 |
| 16 | 680 | 197 | BAA-1717 | 105 | 463500 | 41230 | 86 |
| 17 | 1096 | 178 | BAA-1720 | 111 | 1651000 | 401600 | 70 |
| 18 | 89100 | 1437 | BAA-1720 | 111 | 801100 | 60590 | 90 |
| 19 | 2880 | 158 | BAA-1720 | 111 | 1076000 | 257300 | 38 |
| 20 | 48020 | 195 | BAA-1720 | 111 | 622800 | 59180 | 65 |
| 21 | 1280 | 132 | BAA-1720 | 111 | 805600 | 163400 | 38 |
| 22 | 1446 | 192 | BAA-1720 | 111 | 317000 | 5885 | 82 |
| 23 | 46610 | 165 | BAA-1720 | 111 | 1085000 | 201700 | 52 |
| 24 | 685 | 140 | BAA-1720 | 111 | 835600 | 209800 | 28 |
| 25 | 78950 | 152 | BAA-1763 | 87 | 520600 | 45140 | 41 |
| 26 | 136400 | 160 | BAA-1763 | 87 | 296100 | 34190 | 47 |
| 27 | 3588 | 177 | BAA-1763 | 87 | 804900 | 56840 | 32 |
| 28 | 4231 | 170 | BAA-1763 | 87 | 653000 | 36440 | 38 |
| 29 | 104200 | 157 | BAA-1763 | 87 | 526900 | 59530 | 45 |
| 30 | 662 | 198 | BAA-1763 | 87 | 250200 | 25280 | 37 |
| 31 | 33430000 | 390 | BAA-1763 | 87 | 41320000 | 3571 | 270 |
| 32 | 848600 | 253 | BAA-1763 | 87 | 624500 | 20680 | 141 |
| 33 | 145700 | 4303 | BAA-1766 | 79 | 569900 | 880600 | 205 |
| 34 | 81410 | 265 | BAA-1766 | 79 | 4799000 | 583300 | 190 |
| 35 | 16140 | 202 | BAA-1766 | 79 | 3203000 | 823 | 81 |
| 36 | 36630 | 202 | BAA-1766 | 79 | 5204000 | 539800 | 81 |
| 37 | 372 | 126 | BAA-1766 | 79 | 3717000 | 436100 | 27 |
| 38 | 2223 | 150 | BAA-1766 | 79 | 3976000 | 369900 | 18 |
| 39 | 1160 | 190 | BAA-1766 | 79 | 3502000 | 511100 | 53 |
| 40 | 341 | 171 | BAA-1766 | 79 | 1688000 | 85880 | 75 |

TABLE S5-continued

| CFU and RLU for nasal swabs: endogenous, MRSA spike, and autoluminescence (Table 5) | | | | | | | |
|---|---|---|---|---|---|---|---|
| RLU for Endogenous[1] (Elutant only) | | | RLU for MRSA Spike[2] (Elutant + MRSA) | | | | RLU for Autoluminescence[3] (No luciferase) |
| Swab # | Control | Selective | Strain | CFU[4] | Control | Selective | — |
| BHI | — | — | BAA-1707 | 65 | 2112000 | 900500 | — |
| BHI | — | — | BAA-1717 | 105 | 614300 | 43590 | — |
| BHI | — | — | BAA-1720 | 111 | 245100 | 147900 | — |
| BHI | — | — | BAA-1763 | 87 | 35380 | 6080 | — |
| BHI | — | — | BAA-1766 | 79 | 191300 | 10460 | — |
| BHI | 126 | 85 | — | — | — | — | 22 |

[1]Nasal swabs were eluted in BHI and assayed directly.
[2]Nasal elutants were spiked with the indicated MRSA strain at the stated CFU per well.
[3]Nasal elutants were combined with luciferase substrate and buffer in the absence of luciferase reporter phage. Signal in these wells is considered to be autoluminescence, likely the result of non-specific activation of the substrate or pre-existing luminescence in the sample.
[4]CFU were determined directly by plate counting (in duplicate).

In order to determine if this method could successfully detect MRSA in a nasal matrix, five well-characterized MRSA strains were spiked into the elutants from the previously described 40 non-colonized nasal swabs. RLU and CFU values for each sample are provided (Table S5). The median burden of a MRSA spike was 87 CFU per well. 40 of 40 (100%) MRSA spiked samples were positive in both the control and selective conditions (Table 5). The lack of any invalid samples suggests the absence of assay inhibitors in these individuals. The successful detection of five unique MRSA strains when spiked into these samples at low burdens supports the efficacy of bacteriophage-based screening in nasal matrix.

As shown in the Examples, the present disclosure provides a MRSA luciferase phage reporter assay, in a culture-based approach, that achieves sensitive and rapid detection of MRSA from nasal swabs. As shown in Table 1, a diagnostic screen utilizing MRSA luciferase phage reporter assay was capable of identifying MRSA strains from diverse genetic backgrounds in approximately six hours. For the vast majority of MRSA strains, successful detection required the presence of only 10 to 100 CFU per well, approximately equivalent to 75 to 750 CFU per nasal swab. This limit of detection is similar to previously described PCR-based screens. The median burden of MRSA recovered from nasal swabs of carriers has been found to be greater than 10,000 CFU. Additionally, individuals with high burdens of nasal colonization are more likely to carry MRSA at multiple body sites and be vectors for transmission. The sensitivity of this assay thus appears well-suited to address the expected burden from clinical nasal specimens whether the goal is to eliminate MRSA carriage or limit patient to patient spread.

In some respects, the performance of luciferase reporter phage assays is highly dependent on the selection of bacteriophage. This MRSA diagnostic screen in the Examples utilized NANOLUC® (luciferase)-expressing recombinants of two phage, ISP and MP115, which are members of the Myoviridae family of large lytic staphylococcal bacteriophages. These phages bind to the host surface primarily through highly conserved WTA, resulting in broad-host-range capabilities. Mutants lacking WTA are thought to be resistant to all, or at least most, staphylococcal phages. Although resistant WTA-deficient mutants are hypothetically possible, previous studies have revealed that WTA is required for both nasal colonization and methicillin resistance. Generally, the loss of WTA also results in a fitness cost in vivo and overall decrease in virulence. Therefore, it is reasonable to expect that all current and future MRSA strains involved in nasal carriage will possess the receptor targeted by this screen. Moreover, this conclusion is further supported by the data in Table 4 which shows a positive phage signal detected for 99.5% of clinical MRSA isolates tested.

As shown in the results in Table 4, of the 513 Staphylococcus aureus clinical strains, two isolates of MRSA (BNC 159 and PHX 079) and one isolate of MSSA (MSSA 090) failed to generate a positive signal in the control condition. One of these isolates (PHX 079) appeared to have a growth defect in culture (data not shown). Poor growth during the enrichment period could have contributed to the inability to reliably detect this MRSA strain. The failure to detect BNC 159 and MSSA 090 may be associated with phage resistance through restriction-modification systems or capsule production. Restriction-modification systems target and eliminate foreign DNA, often identified through the presence or absence of DNA methylation at specific motifs. Evidence exists that staphylococcal phages have evolved under the pressure of these pathways, and several phages are entirely devoid of particular sequences targeted by these systems. Despite this, the diversity of restriction-modification systems across Staphylococcus aureus is extensive and may contribute to the resistance seen in these isolates. Separately, capsule production has been linked with phage resistance in Staphylococcus aureus through the masking of surface receptors. While several common lineages of Staphylococcus aureus do not produce capsular polysaccharide, this mechanism could facilitate the rare (<1%) resistance observed.

Additionally, Table 4 also shows that the combination of MRSA luciferase phage reporter assay and a selective agent (e.g., an antibiotic) restricted the viability and growth of non-MRSA, and did not interfere with MRSA detection. For example, the MRSA luciferase phage reporter assay utilized cefoxitin to restrict the viability and growth of non-MRSA. The results in Table 4 evidence the efficacy of this selection, as only 6.5% of clinical MSSA strains were positive when tested at approximately 500 CFU per well. Surprisingly, cefoxitin did not interfere with MRSA detection, as 97.7% of clinical MRSA strains remained positive in selective wells at approximately 50 CFU per well. Additionally, Table 3 shows that this selective agent was also beneficial in restricting the false positives from several species of Bacillus and coagulase-negative staphylococci, while also preventing interference from Streptococcus pneumoniae. Cefoxitin has been demonstrated as a superior choice for MRSA selection, capable of identifying diverse isolates.

Despite the high rate of detection of clinical MRSA, some strains did yield false-negative results in the presence of cefoxitin. Since clinical MRSA strains were evaluated at particularly low burdens in some examples, it is plausible that these strains express low-level resistance or heterore-sistance. Such strains may present a limit of detection greater than 100 CFU per well, similar to that found for BAA-42 (Table 1).

Regarding performance with nasal swabs, Table 5 pro-vides that 90.0% of MRSA-negative samples gave a nega-tive test result under selection and agreed with the reference method. False positives were thus detected in 10% of nasal elutants. These false positives may originate from three sources. First, autoluminescence may occur but was ruled out in these samples by demonstrating a requirement for added luciferase as provided in Table S5. Second, high burdens of certain MSSA strains may result in false positives (Table 4). Finally, some cross-reacting species of coagulase-negative *staphylococci* can become methicillin-resistant through the same resistance mechanism as MRSA. These species could potentially contribute to the weak false MRSA positives observed in four samples.

The methods and systems for detecting MRSA described herein are unique in evaluating the validity of a sample by requiring the viability of endogenous nasal flora. In order to replicate endogenous nasal flora, nasal elutants were spiked with one of five MRSA strains (Table 5). As shown in Table 5, positive detection of low MRSA burdens in nasal matrix was achieved in 100% of spiked samples. Importantly, this indicates that successful bacteriophage infection and lucifer-ase production is capable of occurring in the nasal matrix. Furthermore, this reveals that the negative control wells seen previously in 10% of endogenous samples were not the result of assay inhibitors. Overall, the results strongly sug-gest that MRSA carriage, when present, would be detected in nasal specimens.

The bacteriophage-based MRSA assay described herein is a member of a new generation of luciferase reporter phage systems utilizing NANOLUC® (luciferase) to sensitively detect target species. The method proved to be highly

Example 5. Direct Coating of NanoLuc on Medium and High Protein Binding Plates

*Staphylococcus aureus* (ATCC 12600) was grown to log phase ($OD_{600}$ of 0.41) in tryptic soy broth (TSB). Cultures were diluted in TSB to obtain the desired burden, which was confirmed by plating on TSB agar for colony forming units (CFU). 12.5 µL of each dilution was added directly to 37.5 µL of TSB or human blood in 96-well strips (high binding; (Grenier Bio-One, Ref #762074). When indicated, some strips contained bound anti-NanoLuc antibody (purified mouse monocolonal IgG clone #965808; Catalog #MAB10026) for capture. Human blood was collected from a single donor using sodium heparin as an anti-coagulant. For blood samples, 100 µL of TSB containing sodium polyanethole sulfonate (SPS) was added to achieve a 25% human blood matrix. The final concentration of SPS in the well (150 µL volume) was 0.05%. For TSB samples, 100 µL of TSB was added to achieve the same 150 µL volume. Test strips were then sealed with cover film and incubated at 37° C. for 30 minutes. After this brief enrichment, 20 µL of phage working stock were added to wells containing the TSB matrix. Phage working stock contained $8 \times 10^7$ plaque forming units per mL of both MP115. NL and SAPJV1. NL. To permit infection in wells containing blood matrix, 0.5 mg of recombinant *Staphylococcal* protein A (pro-356, Prospec, Ness-Ziona, Israel) per well was included as indicated within the 20 µL of phage working stock. Assay strips were once again sealed with cover film and incubated at 37° C. for three hours. Following infection, these strips were washed three times with 300 µL PBS-T (10 mM sodium phosphate, 150 mM NaCl, 0.05% Tween 20, pH 7.4). Washes were conducted using an automatic plate washer (AccuWash, Thermo Fisher Scientific, Waltham, MA, USA). 100 µL of NanoGlo buffer (Promega, Madison, WI, USA) containing 1 µL of NanoGlo substrate (Promega, Madison, WI, USA) was added to each well. Following a 3-minute wait period, the signal output of each sample as relative light units (RLU) was determined using a GloMax Navigator (Promega, Madi-son, WI, USA). Signal over background (SB) was calculated by dividing the RLU from each sample from the RLU observed in the media control for that test matrix.

TABLE 6

| Sample | Burden | CFU/well | Test Matrix | Protein A Added During Infection | Anti-NanoLuc Capture Strips | | Control Strips | |
|---|---|---|---|---|---|---|---|---|
| | | | | | RLU | S/B | RLU | S/B |
| *S. aureus* | High | 5150 | TSB | No | 614600 | 15365 | 1100 | 65 |
| *S. aureus* | Low | 52 | TSB | No | 525 | 13 | 7 | 0 |
| Media Control | — | N/A | TSB | No | 40 | 1 | 17 | 1 |
| *S. aureus* | High | 5150 | Blood | No | 75 | 4 | 8 | 1 |
| *S. aureus* | Low | 52 | Blood | No | 17 | 1 | 7 | 1 |
| *S. aureus* | High | 5150 | Blood | Yes | 168800 | 8440 | 13 | 1 |
| *S. aureus* | Low | 52 | Blood | Yes | 562 | 28 | 8 | 1 |
| Media Control | — | N/A | Blood | Yes | 20 | 1 | 12 | 1 | inclusive and, when combined with cefoxitin selection, discriminated against the majority of non-resistant strains. Moreover, the screen was capable of identifying low bur-dens of MRSA in nasal samples with no evidence of problematic interference. Additionally, with MRSA detec-tion made within six hours, actionable results would be available in a single work shift. Ultimately, the data shows that the bacteriophage-based MRSA assay described herein may be a promising new tool for the detection of MRSA colonization from nasal swabs.

In these examples, the anti-NANOLUC® (anti-luciferase) antibody is the immobilized binding partner. Table 6 dem-onstrates a substantial increase in signal detection when the indicator protein is captured by an immobilized binding partner. For example, in samples with a low burden or high burden of *S. aureus*, the RLU is significantly higher when the indicator protein is captured by the anti-NANOLUC® (anti-luciferase) antibody than when the sample is not cap-tured using the control strips. Surprisingly, no infection of the *S. aureus* can take place if the *S. aureus* has bound IgG.

The addition of Protein A allows *S. aureus* to be infected. Red blood cells and other serum proteins do not interfere with the capture of expressed indicator protein. Additionally, quenching of the signal as seen in the control by the red blood cells is eliminated and signal over background is maintained or increased. Thus, the indicator protein can be detected using whole blood samples with minimal interference from other components in the sample (e.g., proteins). Conventionally, serum or plasma is isolated from the blood for reliable detection of the indicator protein product. Advantageously, the examples demonstrate that the methods of detection can be done on whole blood samples taken directly from a patient by using this capture step.

Example 6. Antibiotic Susceptibility Testing in Human Blood

Methicillin-resistant *Staphylococcus aureus* (MRSA) strains (ATCC BAA-1720, CDC AR0480) and methicillin-susceptible *Staphylococcus aureus* (MSSA) strain (ATCC 12600) were grown to log phase (OD600 ranged from 0.16 to 0.4) in tryptic soy broth (TSB). Cultures were diluted in TSB to obtain the desired burden, which was confirmed by plating on TSB agar for colony forming units (CFU). 50 μL of each dilution was added to test strips. When indicated, some strips contained bound anti-NANOLUC® (anti-luciferase) antibody (purified mouse monoclonal IgG clone #965808; Catalog #MAB10026) on medium-binding plates (Grenier Bio-One, Strips Plate 12×F8, PS, F-Bottom, White, Lumitrac, Med Binding, Ref #762075) or high-binding plates (Grenier Bio-One, Ref #762074) for capture. 85 μL of ing units per mL (pfu/mL) of MP115.NL and 6.9×108 pfu/mL of SAPJV1.NL. For wells containing blood matrix, 0.5 mg of recombinant *Staphylococcal* protein A (pro-356, Prospec, Ness-Ziona, Israel) per well was included within the 20 μL of phage working stock. Assay strips were once again sealed with cover film and incubated at 37° C. for three hours. Following infection, anti-NANOLUC® (anti-luciferase) capture and controls strips were washed three times with 300 μL PBS-T (10 mM sodium phosphate, 150 mM NaCl, 0.05% Tween 20, pH 7.4). Washes were conducted using an automatic plate washer (AccuWash, Thermo Fisher Scientific, Waltham, Mass., USA). 100 μL of NANO-GLO® (an imidazopyrazinone substrate (furimazine) buffer (Promega, Madison, Wis., USA) containing 1 μL of NANO-GLO® substrate (an imidazopyrazinone substrate (furimazine)) (Promega, Madison, Wis., USA) was added to each well. "No wash+No Capture" strips were not washed and instead received 65 μL of a master mix containing 50 μL NANO-GLO® (an imidazopyrazinone substrate (furimazine)) Buffer, 15 μL TSB, and 1 μL NANO-GLO® substrate (an imidazopyrazinone substrate (furimazine)). 5% BSA blocked strips (bovine serum albumin, Sigma Life Science Product #A9647) were washed. The BSA blocked strips were blocked with BSA for non-specific binding sites. Following a 3-minute wait period, the signal output of each sample as relative light units (RLU) was determined using a GLOMAX® Navigator (luminometer) (Promega, Madison, Wis., USA). Signal over background (SB) was calculated by dividing the RLU from each sample from the RLU observed in the media control for that test matrix.

TABLE 7

| No Capture + No Wash | | | TSB | | TSB + FOX | | Blood | | Blood + FOX | |
|---|---|---|---|---|---|---|---|---|---|---|
| Sample | Susceptibility | CFU/Well | RLU | S/B | RLU | S/B | RLU | S/B | RLU | S/B |
| BAA-1720 (MRSA) | Resistant | 41 | 168400 | 208 | 342000 | 447 | 29440 | 775 | 9035 | 177 |
| AR0480 (MRSA) | Resistant | 110 | 631600 | 779 | 127000 | 166 | 36890 | 971 | 432 | 8 |
| 12600 (MSSA) | Susceptible | 130 | 393100 | 485 | 988 | 1 | 42810 | 1127 | 103 | 2 |
| Media (Control) | N/A | N/A | 811 | 1 | 765 | 1 | 38 | 1 | 51 | 1 |

| Anti-NanoLuc Capture Strips | | | TSB | | TSB + FOX | | Blood | | Blood + FOX | |
|---|---|---|---|---|---|---|---|---|---|---|
| Sample | RLU | S/B | RLU | S/B | RLU | S/B | RLU | S/B | RLU | S/B |
| BAA-1720 (MRSA) | Resistant | 41 | 53610 | 623 | 79180 | 1028 | 112900 | 6272 | 63960 | 3998 |
| AR0480 (MRSA) | Resistant | 110 | 137700 | 1601 | 96650 | 1255 | 286400 | 15911 | 6927 | 433 |
| 12600 (MSSA) | Susceptible | 130 | 95180 | 1107 | 80 | 1 | 330900 | 18383 | 18 | 1 |
| Media (Control) | N/A | N/A | 86 | 1 | 77 | 1 | 18 | 1 | 16 | 1 |

| 5% BSA Blocked Strips | | | TSB | | TSB + FOX | | Blood | | Blood + FOX | |
|---|---|---|---|---|---|---|---|---|---|---|
| Sample | RLU | S/B | RLU | S/B | RLU | S/B | RLU | S/B | RLU | S/B |
| BAA-1720 (MRSA) | Resistant | 41 | 210 | 35 | 20 | 3 | 21 | 2 | 12 | 2 |
| AR0480 (MRSA) | Resistant | 110 | 51 | 9 | 53 | 7 | 16 | 2 | 3 | 0 |
| 12600 (MSSA) | Susceptible | 130 | 120 | 20 | 6 | 1 | 15 | 2 | 10 | 1 |
| Media (Control) | N/A | N/A | 6 | 1 | 8 | 1 | 10 | 1 | 8 | 1 | either TSB or human blood diluted with TSB and sodium polyanethole sulfonate (SPS) was added. Human blood was collected from a single donor using sodium heparin as an anti-coagulant. Each well then received 15 μL of either TSB or 22 μg/mL cefoxitin (FOX) in TSB. The final concentration of each component in the well (150 μL volume) was 25% human blood, 0.0375% SPS, and 2.2 μg/mL FOX. Test strips were then sealed with cover film and incubated at 37° C. for two hours. After this selective enrichment, 20 μL of phage working stock was added to wells containing the TSB matrix. Phage working stock contained 8×107 plaque form- In Table 7, the examples for "No Capture+No Wash" demonstrated the total signal generated and the drop in signal due to cefoxitin when the assay is done in just media (TSB). When done in the presence of blood, the signal is quenched. When the capture strips are used, there is a substantial increase in signal due to removal of the quenching done by blood. The 5% BSA blocked strip (bovine serum albumin, Sigma Life Science Product #A9647) is to show non-specific binding. Once again, the examples demonstrate a substantial increase in signal detection when the indicator protein was captured by an immobilized binding partner for whole blood samples. Additionally, the signal detection was significantly improved by the capture step for whole blood samples that included an antibiotic. Surprisingly, the indicator protein can be detected using whole blood samples with minimal interference from other components in the sample.

Example 7. Titration of NANOLUC® (Luciferase) Coated Plates

A stock solution of purified NANOLUC at 1.5 mg/mL was diluted to 1 ng/ml in PBS. Serial 10 fold dilutions in PBS were made from the 1 ng/ml to 0.001 pg/mL. Rabbit anti mouse IgG (Abeam, Catalog #46540) or goat anti mouse IgG (Abeam, Catalog #6708) were diluted in PBS to Antibody coated strips were washed three times with 300 L/well PBS-T (10 mM sodium phosphate, 150 mM NaCl, 0.05% Tween 20, pH 7.4). Washes were conducted using an automatic plate washer (AccuWash, Thermo Fisher Scientific, Waltham, Mass., USA). 100 μL of NANO-GLO® ((an imidazopyrazinone substrate (furimazine)) buffer (Promega, Madison, Wis., USA) containing 1 μL of NANO-GLO® substrate (an imidazopyrazinone substrate (furimazine)) (Promega, Madison, Wis., USA) was added to each well. Following a 3 minute wait period, the signal output of each sample as relative light units (RLU) was determined using a GLOMAX® Navigator (luminometer) (Promega, Madison, Wis., USA). Signal over background (SB) was calculated by dividing the RLU from each sample from the RLU observed in the PBS control for that test.

TABLE 8

| Coating Conditions | No Wash | | Washed | | | | | |
|---|---|---|---|---|---|---|---|---|
| | NanoLuc Input only | NanoLuc Input only | Mouse Anti-NanoLuc | Mouse Anti-NanoLuc | Rabbit AB | Rabbit AB | Goat AB | Goat AB |
| MsxNanoLuc Antibody (ug/well) | 0 | 0 | 0.1 | 0.1 | 0.1 | 0.1 | 0.1 | 0.1 |
| Plate PBS | Medium RLU | Medium S/B | Medium RLU | Medium S/B | Medium RLU | Medium S/B | Medium RLU | Medium S/B |
| | 32 | 1 | 31 | 1 | 32 | 1 | 28 | 1 |
| $3 \times 10^3$ mol/well | 32 | 1 | 39 | 1.3 | 20 | 0.6 | 26 | 0.9 |
| $3 \times 10^4$ mol/well | 32 | 1 | 27 | 1.3 | 24 | 0.6 | 30 | 0.9 |
| $3 \times 10^5$ mol/well | 289 | 9 | 44 | 1.4 | 41 | 1.3 | 64 | 2.3 |
| $3 \times 10^6$ mol/well | 2693 | 84.2 | 101 | 3.3 | 198 | 6.2 | 312 | 11.1 |
| $3 \times 10^7$ mol/well | 32027 | 1000.8 | 1025 | 33.1 | 1661 | 51.9 | 4336 | 154.9 |
| $3 \times 10^8$ mol/well | 361334 | 11291.7 | 7989 | 257.7 | 18328 | 572.8 | 47652 | 1701.9 |
| $3 \times 10^9$ mol/well | 4212035 | 131626.1 | 85459 | 2756.7 | 239180 | 7474.4 | 515210 | 18400.4 |
| MsxNanoLuc Antibody (ug/well) | 0 | 0 | 0.1 | 0.1 | 0.1 | 0.1 | 0.1 | 0.1 |
| Plate PBS | High RLU | High S/B | High RLU | High S/B | High RLU | High S/B | High RLU | High S/B |
| | 39 | 1 | 32 | 1 | 32 | 1 | 100 | 1 |
| $3 \times 10^3$ mol/well | 29 | 0.7 | 32 | 1 | 58 | 1.8 | 34 | 0.3 |
| $3 \times 10^4$ mol/well | 32 | 0.7 | 31 | 1 | 33 | 1.8 | 25 | 0.3 |
| $3 \times 10^5$ mol/well | 29 | 0.7 | 28 | 0.9 | 46 | 1.4 | 68 | 0.7 |
| $3 \times 10^6$ mol/well | 28 | 0.7 | 90 | 2.8 | 241 | 7.5 | 319 | 3.2 |
| $3 \times 10^7$ mol/well | 36 | 0.9 | 694 | 21.7 | 2234 | 69.8 | 12232 | 122.3 |
| $3 \times 10^8$ mol/well | 78 | 2 | 6813 | 212.9 | 18033 | 563.5 | 105519 | 1055.2 |
| $3 \times 10^9$ mol/well | 577 | 14.8 | 78499 | 2453.1 | 1352697 | 42271.8 | 1673864 | 16738.6 |

10 μg/mL and pipetted into 100 μL/wells. The plates were incubated at 2-8° C. for 18-20 hours and then washed 3 times with 300 μL of PBS/well/wash. The mouse anti-NANOLUC® (anti-luciferase) antibody (purified mouse monoclonal IgG, clone #965808, R&D Systems, Catalog #MAB10026) is diluted to 1 μg/mL in PBS and pipetted into 100 μL/well to the plates coated with Rabbit or Goat anti mouse IgG. A 5% BSA blocked strip was included for non-specific binding determination and an uncoated strip for Nanoluc activity measurement. Assay strips were sealed with cover film and incubated at 37° C. for three hours.

Tables 8 and 9 demonstrate that the plates coated with rabbit anti mouse IgG or goat anti mouse IgG provided an improved orientation of the mouse anti-NANOLUC® (anti-luciferase) for improved capture/binding surface. In fact, the plates coated with rabbit anti mouse IgG or goat anti mouse IgG provides higher availability for binding an indicator protein product. The coating of the plates exhibited improved signal detection, which may be due to the orientation of the mouse anti-NANOLUC® (anti-luciferase) and the availability of the binding sites to the indicator protein.

The present disclosure is not limited to the exact details shown and described, for variations obvious to one skilled in the art will be included within the present disclosure defined by the claims.

That which is claimed is:

1. A method for detecting Methicillin-resistant *Staphylococcus aureus* (MRSA) in a sample, the method comprising:
   obtaining a whole blood sample;
   adding a selective agent to the whole blood sample, wherein the selective agent comprises an antibiotic;
   contacting the whole blood sample with a cocktail comprising one or more recombinant bacteriophages, wherein at least one of the recombinant bacteriophages comprises a genetically modified *Staphylococcus aureus*-specific bacteriophage genome including an indicator gene and is specific to *Staphylococcus aureus*, and wherein the indicator gene encodes a soluble luciferase;
   capturing the soluble luciferase with a substrate comprising an immobilized binding partner;
   washing the substrate including the captured soluble luciferase to remove any uncaptured microorganisms; and
   detecting a signal produced by the soluble luciferase, wherein detection of the signal is used to determine presence of MRSA in the whole blood sample, and wherein a ratio of the signal to background is at least 2.0.

2. The method of claim 1, wherein the antibiotic comprises a cephalosporin-based antibiotic.

3. The method of claim 1, wherein the indicator gene is codon-optimized.

4. The method of claim 3, wherein the at least one of the recombinant bacteriophages comprises an untranslated region upstream of the indicator gene, wherein the untranslated region includes a bacteriophage late gene promoter.

5. The method of claim 1, wherein the capturing step comprises contacting the soluble luciferase with a surface.

6. The method of claim 5, wherein the surface is a microtiter plate, latex particle, lateral flow strip, bead, magnetic particle, or dipstick.

7. The method of claim 5, further comprising depositing the immobilized binding partner on the surface before capturing the soluble luciferase.

8. The method of claim 7, wherein the immobilized binding partner is an antibody or a fragment thereof.

9. The method of claim 7, further comprising washing the surface comprising the immobilized binding partner.

10. The method of claim 9, further comprising washing the surface after capturing the soluble luciferase.

11. The method of claim 1, wherein the whole blood sample is first incubated in conditions favoring growth for an enrichment period of less than 24 hours, 23 hours, 22 hours, 21 hours, 20 hours, 19 hours, 18 hours, 17 hours, 16 hours, 15 hours, 14 hours, 13 hours, 12 hours, 11 hours, 10 hours, 9 hours, 8 hours, 7 hours, 6 hours, 5 hours, 4 hours, 3 hours, or 2 hours.

* * * * *